(12) United States Patent
Boy et al.

(10) Patent No.: US 8,785,154 B2
(45) Date of Patent: Jul. 22, 2014

(54) METHOD FOR MANUFACTURING AN AQUEOUS GLUCOSE SOLUTION FROM PLANTS OF THE TRITICEAE SPECIES

(75) Inventors: Matthias Boy, Bensheim (DE); Stephan Freyer, Neustadt (DE); Julia Brodersen, Hamburg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/937,554

(22) PCT Filed: Apr. 9, 2009

(86) PCT No.: PCT/EP2009/054298
§ 371 (c)(1),
(2), (4) Date: Oct. 13, 2010

(87) PCT Pub. No.: WO2009/127593
PCT Pub. Date: Oct. 22, 2009

(65) Prior Publication Data
US 2011/0033896 A1 Feb. 10, 2011

(30) Foreign Application Priority Data
Apr. 14, 2008 (EP) .................................... 08154482

(51) Int. Cl.
*C12P 21/02* (2006.01)

(52) U.S. Cl.
USPC .......................................... 435/71.1; 426/656

(58) Field of Classification Search
CPC .................................. A23K 1/007; C13K 1/06
USPC ........................................... 435/71.1; 426/18
See application file for complete search history.

(56) References Cited

U.S. PATENT DOCUMENTS

| | | | |
|---|---|---|---|
| 4,094,700 | A | 6/1978 | Rennes et al. |
| 4,171,384 | A | 10/1979 | Chwalek et al. |
| 4,287,304 | A | 9/1981 | Muller et al. |
| 4,311,714 | A * | 1/1982 | Goering et al. ................ 426/28 |
| 2009/0162892 | A1 | 6/2009 | Pompejus et al. |
| 2009/0226571 | A1 | 9/2009 | Freyer et al. |
| 2010/0196964 | A1 | 8/2010 | Boy et al. |

FOREIGN PATENT DOCUMENTS

| | | |
|---|---|---|
| CN | 1173541 A | 2/1998 |
| CN | 1590553 A | 3/2005 |
| DE | 2642628 A1 | 3/1977 |
| GB | 1153291 * | 5/1969 |
| GB | 1153291 A | 5/1969 |
| WO | WO-2005/116228 A2 | 12/2005 |
| WO | WO-2006/119206 A2 | 11/2006 |
| WO | WO-2007/028804 A1 | 3/2007 |
| WO | WO-2009/007326 A2 | 1/2009 |

OTHER PUBLICATIONS

Graybosch et al., Trends in Food Science & Technology, vol. 9, No. 4, p. 135-142, 1998.*
Koutinas et al., Biotechnology and Bioengineering, vol. 85, No. 5, p. 524-538, 2004.*
Daniel, J.R., et al., "Starch and Other Polysaccharides", Ullmann's Encyclopedia of Industrial Chemistry, vol. A25, (1994), pp. 1-62.
McAloon, A., et al., "Determining the Cost of Producing Ethanol from Corn Starch and Lignocellulosic Feedstocks", NREL/TP-580-28893, (2000), pp. 1-44.
Koutinas, A.A., et al., "Restructuring Upstream Bioprocessing: Technological and Economical Aspects for Production of a Generic Microbial Feedstock from Wheat", Biotechnology and Bioengineering, vol. 85, No. 5, (2004), pp. 524-538.
Koutinas, A.A., "Polyhydroxybutyrate Production from a Novel Feedstock Derived from a Wheat-Based Biorefinery", Enzyme and Microbial Technology, vol. 40, No, 5, (2007), pp. 1035-1044.
"Alcohol Cleaning Production Technology Using Wheat as Raw Material", WPI Thomson, No. AN 2005-488945, XP-002563917, CN1590553, Mar. 9, 2005.
Jacques, K., et al. (eds.), "The Alcohol Textbook—A Reference for the Beverage, Fuel, and Industrial Alcohol Industries", 3$^{rd}$ edition, Nottingham Univ. Press, Chapter 2, (1995), pp. 7-23.

* cited by examiner

*Primary Examiner* — Susan Hanley
*Assistant Examiner* — Damon B Bowe
(74) *Attorney, Agent, or Firm* — Drinker Biddle & Reath LLP

(57) ABSTRACT

The present invention relates to a method for manufacturing an aqueous glucose solution from the starch components of Triticeae grains, for example from rye, triticale or in particular wheat grains. The invention also relates to a glucose-based fermentation method for manufacturing organic compounds in which the glucose manufactured for fermentation is produced from the starch components of Triticeae grains by way of a method according to the invention.

23 Claims, No Drawings

METHOD FOR MANUFACTURING AN AQUEOUS GLUCOSE SOLUTION FROM PLANTS OF THE TRITICEAE SPECIES

RELATED APPLICATIONS

This application is a national stage application (under 35 U.S.C. §371) of PCT/EP2009/054298, filed Apr. 9, 2009, which claims benefit of European application 08154482.7, filed Apr. 14, 2008.

The present invention relates to a method for producing an aqueous glucose solution from the starch components of Triticeae grains, for example from rye, triticale or, in particular, wheat grains. The invention also relates to a glucose-based fermentation method for producing organic compounds in which the glucose produced for fermentation is produced by a method according to the invention from the starch components of Triticeae grains.

Glucose, and in particular aqueous glucose solutions, are a basic carbon source for many chemical and fermentation methods for producing organic products. For example, during fermentation, the glucose molecules are metabolized by the microorganisms used and converted in this way into the desired organic valuable product. The range of organic products produced in this manner comprises, for example, low-molecular-weight volatile compounds such as ethanol, aliphatic carboxylic acids, amino acids, vitamins, carotenoids, sugar alcohols, sugar acids and polyols, and also enzymes and organic polymers.

Differing carbon sources are used for such generally known fermentation methods, depending on the process conditions and the products which are to be produced. Said carbon sources range from pure sucrose through sugar beet molasses and sugar cane molasses, glucose from starch hydrolyzates, to glycerol.

In the conventional production of glucose from starch, first the starch is isolated from a natural starch source such as potatoes, cassava, cereals, for example wheat, corn, barley, rye, triticale or rice, and subsequently hydrolyzed, generally by an enzymatic liquefaction, followed by an enzymatic saccharification.

In the production of glucose by liquefying and saccharifying starch, generally material used is a prepurified starch, i.e. the natural starch sources such as potatoes, cassava and cereals, for example wheat, corn, barley, rye, triticale or rice, are fractionated into the starch components and the non-starch components before the liquefaction/saccharification.

A central problem in isolating starch from grains of Triticeae plants (hereinafter Triticeae grains) is separating off the gluten. Unlike in the case of isolating corn starch from corn kernels, in which the gluten is extracted together with the starch during steeping of the kernels, the gluten from Triticeae grains sticks the grains together during steeping and encloses the starch.

The isolation of the starch from Triticeae, in particular from wheat, currently proceeds generally by the Martin method or a modified Martin method, termed the batter method (see in this context J. R. Daniel et al., "Starch and other Polysaccharides" in Ullmanns Encyclopedia of Industrial Chemistry, 5th ed. on CD-ROM). In the Martin method, the grains of the Triticeae plants are first milled by a dry milling method to form a flour, wherein the majority of the husk components (bran) are separated off. Subsequently the flour is kneaded with about 0.5 part by weight of water per part by weight of flour to form a dough, from which, after a standing time, the starch components are extracted by rinsing with water. Residual fibers and gluten components are separated off from the starch suspension thus obtained. The batter method differs therefrom in that, for producing the dough, about 1 part by weight of water is used per part by weight of flour, and subsequently the dough is suspended in twice the amount of water and the gluten and residual fiber components are removed from this suspension by screening. In both cases a dilute starch suspension is obtained which is subsequently fed to a liquefaction/saccharification for producing glucose. In this manner a very pure glucose is obtained. The gluten which is separated off is dried and marketed as what is termed vital gluten.

The methods of the prior art for isolating starch, however, are relatively complex and are associated with high production of waste water. Moreover, the by-products and waste products produced in the isolation of starch such as proteins (gluten), and sprout and fiber components need to be dried before further processing, which is associated with a considerable consumption of energy. In addition, the apparatus requirement is high and corresponding systems are therefore very capital intensive. Since, on the other hand, cereals and, in particular, wheat are important starch sources, there has been no lack of attempts to provide more favorable alternatives for isolating from these starch sources a glucose which is suitable for fermentation processes.

In order to make the starch components of cereals utilizable, the cereal flour produced by dry milling which, in addition to the components of the endosperm (starch, fat, protein, i.e. gluten), further generally contains fiber components from the husk can in principle be fed as a whole to an enzymatic liquefaction/saccharification. In this manner an aqueous glucose is obtained which contains large amounts of insoluble solids which result from non-starch components of the cereal. Methods for producing glucose by dry milling of cereals with subsequent liquefaction/saccharification are known and are described, for example, in "The Alcohol Textbook—A reference for the beverage, fuel and industrial alcohol industries", Jaques et al. (Ed.), Nottingham Univ. Press 1995, ISBN 1-8977676-735, chapter 2, pages 7 to 23, and in McAloon et al., "Determining the cost of producing ethanol from corn starch and lignocellulosic feedstocks", NREL/TP-580-28893, National Renewable Energy Laboratory, October 2000.

The glucose obtained by saccharification of the entire milled material is utilized to date on an industrial scale only for producing bioethanol. The reasons for this are a plurality of disadvantages which are inherent to this method: firstly the high fraction of insoluble components in the aqueous glucose produced in this manner has the consequence that the viscosity of the aqueous glucose is high even at low glucose concentrations and the aqueous glucose, in addition, is pseudoplastic. Therefore the maximum glucose concentration in an aqueous glucose produced in such a manner generally remains restricted to 30% by weight. Whereas high glucose concentrations are unnecessary for production of bioethanol by fermentation, or, owing to the toxicity of the ethanol formed in the fermentation, are even a problem, a low glucose concentration in the production of other chemicals leads to an unwanted increase in the volumetric flow rate. In addition, the insoluble components can have an adverse effect on a fermentation, for example with regard to the oxygen transfer rate and/or the oxygen demand of the microorganisms used for the fermentation. In addition, these solids can make the subsequent workup and isolation of the product produced by fermentation significantly more difficult. These problems play only a subordinate role in the production of bioethanol by anaerobic fermentation, followed by separation by distillation. Furthermore, it is disadvantageous that the gluten fraction which in wheat, for example, makes up around 20% by weight of the components contained in wheat is not utilized and in addition pollutes the waste water streams.

Recently, various reports have been made of the use of a glucose produced by a dry milling method in the production of fine chemicals by fermentation (see WO 2005/116228 and WO 2007/028804). The method of dry milling with subsequent liquefaction/saccharification described in these applications permits the production of an aqueous glucose having an increased sugar concentration without requiring the insoluble solids contained in the starch source to be separated off. The use of a glucose produced in this way, however, leads in some cases to an inhibition or retardation of the multiplication of the microorganisms.

As already described above, an aqueous glucose which was produced by liquefaction/saccharification of the entire milled material resulting from a dry milling, in addition to the fermentable sugar components, contains large amounts of insoluble solids which are unfermentable. When such an aqueous glucose is used in a fermentation, whether for the production of bioethanol or for the production of fine chemicals, these solids are passed through the fermentation method and thereby increase the volumetric flow rate. After separating off the fermentation product they remain as solid which must be disposed of or at any rate can be used as animal feed. Since the unfermentable components, however, themselves in part are products of value, various reports have been made of separating off some or all of these components before the fermentation.

Various methods have thus been described in which the gluten component of the flour is removed after the liquefaction and before the saccharification (see e.g. U.S. Pat. No. 4,287,304 and CN 1173541). The applicants own investigations have found that separating off the insoluble components at the stage of liquefied starch is problematic and complex and is associated with glucose losses. Such methods have not been described for flour from grains of Triticeae plants such as wheat.

However, in particular in Europe, in addition to corn, in particular also Triticeae plants such as wheat, rye and triticale are of interest as starch sources. However, to date, with the exception of the methods described at the outset for bioethanol production, only those methods have been described in which the starch components of the Triticeae grains have been prepurified.

The object of the present invention is to provide a method for producing a concentrated aqueous glucose having a glucose content of at least 32% by weight, in particular at least or above 35% by weight from Triticeae grains, which method does not have the disadvantages of the prior art. In particular, the resultant glucose should be suitable not only for producing bioethanol, but above all also for the production therefrom of various fine chemicals. The method, in particular, should permit the coupled product gluten to be obtained without great glucose losses.

These and other objects are achieved by the method described hereinafter.

The present invention therefore relates to a method for producing an aqueous glucose solution having a glucose content of at least 32% by weight from the starch components of grains of Triticeae plants, which comprises the following steps:
  a) fractionating dry milling of the grains, wherein the grains are separated into a starch-comprising endosperm fraction (flour) and a bran fraction;
  b) converting the endosperm fraction into an aqueous suspension;
  c) liquefying and enzymatically saccharifying the starch components of the aqueous suspension, obtaining an aqueous glucose, wherein the aqueous suspension has a starch content of at least 30% by weight;

wherein the gluten proportion present in the endosperm fraction is depleted from the aqueous glucose obtained in step c) and/or from the aqueous suspension of the endosperm fraction before carrying out step c).

The method according to the invention is associated with a number of advantages. The first is the apparatus resources required, but also the energy expenditure for producing an aqueous glucose solution by the method according to the invention is very much less than according to the conventional method. In addition, the glucose obtainable by the method according to the invention is particularly suitable as a carbon source for fermentation methods for producing chemicals. The suitability thereof is not only significantly better than that of a glucose solution which is obtainable by liquefying/saccharifying the entire milled material, but, compared with pure glucose or a glucose which is obtainable by liquefying and saccharifying purified starch, leads in a number of microorganisms to better growth of the microorganisms used for the fermentation and/or to higher yields, based on the glucose used. In addition, by means of the method according to the invention, glucose solutions having a high glucose concentration can be produced. The viscosity properties of a glucose obtainable according to the invention are significantly superior to those of a glucose which was produced by liquefying/saccharifying the entire milled material.

The expressions "bran" or "husk" are taken to mean the hard outer hull of the Triticeae grains, the pericarp (generally <10% by weight of the grain). "Bran components" or "husk components" are fragments or parts thereof. The "bran fraction" or "husk fraction" comprises essentially fractions of the bran or of the husk, but can also comprise other components of the grain, in particular parts of the endosperm.

The expression "endosperm" is taken to mean the primarily starch-comprising part of the Triticeae grains (generally 70 to 85% by weight of the grain). The "endosperm fraction" comprises essentially parts of the endosperm, but can also comprise other components, e.g. parts of the bran.

The expression "gluten" is taken to mean the protein components of the Triticeae grains. This protein component is located essentially in the endosperm. The protein proportion in the Triticeae grains depends obviously on the type and variety of the respective Triticeae plant and is typically in the range from 6 to 13% by weight, based on the endosperm, and about 8 to 20% by weight, based on the entire grain.

The glucose solutions produced by the method according to the invention have a characteristic composition which glucose solutions that were produced in other ways do not have. They are therefore novel and are likewise subject matter of the present invention.

In the method according to the invention, the gluten proportion of the endosperm fraction is depleted. The depletion can be carried out not only before step c) is carried out, i.e. before the liquefaction in step c), but also from the glucose obtained in step c), i.e. after the saccharification in step c).

In a preferred embodiment, at least a subquantity of the gluten is separated off from the glucose obtained in step c) (as a further step d)). The amount of gluten depleted from the glucose is preferably at least 30% by weight, in particular at least 40% by weight, e.g. 30 to 100% by weight, in particular 40 to 100% by weight, based on the total amount of gluten depleted in the method according to the invention.

It is likewise possible to deplete the gluten before carrying out step c), i.e. from an aqueous suspension of the endosperm fraction. In this case, however, generally only a subquantity of the gluten is removed from the endosperm fraction which is fed to step c). The amount of gluten depleted before step c) will generally not exceed 70% by weight, in particular 60% by weight, based on the total amount of gluten depleted in the method according to the invention and is, e.g., 10 to 70% by weight, in particular 20 to 60% by weight, based on the total amount of gluten depleted in the method according to the invention. According to a further embodiment, therefore, partial gluten depletion is carried out before carrying out step c) and a gluten depletion is carried out from the aqueous glucose obtained in step c).

The gluten components which can be obtained in the method according to the invention in the case of a separation before carrying out step c) can be utilized and marketed as what is termed vital gluten.

The gluten components which are obtained in the method according to the invention during a separation from the glucose are, in contrast, novel and are distinguished by particular qualities which differentiate them from the gluten components which are obtained in other methods and make them suitable for many applications. Accordingly, the present invention also relates to the gluten occurring in step d).

Step a):

In step a) of the method according to the invention, Triticeae grains are subjected to a fractionating dry milling. The fractionating milling serves to comminute the Triticeae grains and to separate the grain into its components, namely germ, endosperm and husk components (hereinafter also called bran components).

Generally, the grains from Triticeae plants are grains from wheat, rye or triticale, or mixtures of these grains. Preference is given to grains from wheat, in particular to those from soft wheat varieties. However hard wheat varieties are also suitable.

According to the invention, at this stage, the majority, i.e. at least 70% by weight, in particular at least 80% by weight, of the husk components present in the Triticeae grains are separated off from the remaining components of the grain, i.e. endosperm, as a high-fiber bran fraction. The endosperm fraction comprises essentially the starch and protein components of the Triticeae grains, and also remainders of the bran fraction. The bran fraction in turn comprises essentially, i.e. at least 60% by weight, in particular at least 80% by weight, of the husk components present in the grains, and also up to 25% of the endosperm fraction.

Preferably, the endosperm fraction, after the depletion, comprises not more than 20% by weight, in particular not more than 10% by weight, particularly preferably not more than 5% by weight, especially not more than 2% by weight or not more than 1.5% by weight of bran components (crude fiber), based on the total amount of components of the endosperm fraction, other than water, e.g. 0.1 to 20% by weight, frequently 0.1 to 10% by weight, in particular 0.2 to 5% by weight, and particularly preferably 0.3 to 2% by weight, or 0.3 to 1.5% by weight.

In order to avoid starch losses, the bran fraction can be fed to a further workup for separating off the endosperm components which are recirculated to the method according to the invention. Alternatively, it is possible to feed the bran fraction to another use and to feed to the liquefaction/saccharification in step b) only the endosperm fraction and optionally small amounts of bran, i.e. less than 20% by weight, based on the bran components present in the Triticeae grains.

For the fractionating dry milling of the Triticeae grains in step a), the Triticeae grains as they are delivered can be used. However, preferably, cleaned Triticeae grains are used. In the cleaning, not only coarse contaminants, for example wood pieces, plant components such as stems or leaves, stones, glass fragments, screws etc., but also fine contaminants such as broken Triticeae grains, foreign seeds, small stones, sand, are separated off from the Triticeae grains. The separation can be performed in a manner known per se, e.g. by sieving, sifting, or combinations of these measures. Generally, in this case a procedure is followed such that first coarse particles are separated off from the Triticeae grains and the fine contaminants, and then the finely divided particles are separated off from the Triticeae grains. Coarse particles are considered to be those, the particle size of which is at least above a limit of 15 to 20 mm. Finely divided particles are considered to be those, the maximum particle size of which does not exceed a value of 1.5 to 3.5 mm.

Since the fine contaminants, in addition to sand and dust components, also comprise broken Triticeae grains, it is advantageous if the fine contaminants are again subjected to a fractionation. For this, the fine contaminants are separated into a first fraction having a maximum particle size of 0.5 to 2.5 mm, which comprises essentially sand and other dusty material, and a somewhat coarser fraction having particle sizes of at least 2.5 to 3.5 mm, which comprises essentially small or broken Triticeae grains. The latter fraction can be fed back to the cleaned grain for reducing the starch losses. The first fraction can be added to the bran fraction which is yielded in the fractionation.

The Triticeae grains thus cleaned are subsequently subjected to the fractionating dry milling. The fractionating milling is performed in a manner known per se. Generally the dry milling is divided into a first milling stage in which the husk is removed and separation into an endosperm fraction and a bran fraction is performed, and a second milling stage in which the endosperm fraction is milled to the desired particle size. It is obvious to a person skilled in the art that separation is generally not complete, but is only carried out to the desired purity of the fractions, i.e. the endosperm fraction, after separating off the germ, generally still comprises up to 30% by weight, preferably no greater than 20% by weight, of the husk components present in the grain.

In the first stage which is frequently also called dehulling or debranning, the Triticeae grains are comminuted, e.g. by roller mills. The first stage can be carried out as one milling step (milling passage) and is preferably carried out in a plurality of milling steps. Subsequently to one milling passage, the milled material is then separated in a manner known per se into an endosperm fraction, and a bran fraction. In this case, generally, a procedure is followed such that first separation into an endosperm fraction and a bran fraction is performed, which bran fraction still comprises some of the endosperm fraction. The bran fraction which is separated off and comprises some of the endosperm is separated into its components in a second milling passage. Since the endosperm components of the milled material generally have smaller particle sizes than the particles of the bran fraction of the milled material, the first separation can be performed in a simple manner by a sieving method or by sifting. Of course, the individual separation steps can comprise combinations of these measures.

For step a) it has proved to be advantageous when the grains have a certain moisture content which is generally in the range from 10 to 30% by weight, frequently in the range from 10 to 25% by weight, and in particular in the range from 13 to 20% by weight, based on the total weight of the grains. Accordingly, grains which do not have the desired moisture content are admixed with a certain amount of water before or during the dry milling. After the addition of water, the wheat is stored before the further processing, preferably over a period of 0.5 to 36 h, whereby the moisture adhering to the surface can diffuse into the interior of the grain. Therefore, the milling in step a) is generally carried out in the presence of 10 to 30% by weight, frequently 10 to 25% by weight, of water based on the mass of the Triticeae grains used. Preferably, the amount of water is 13 to 20% by weight, and in particular 14 to 18% by weight. The water is preferably added before the first milling stage, but can also be added during the first milling stage. In the case of a multistage procedure of the first milling stage, the water content can be adjusted once more between the respective milling steps. The water can also optionally be added in the vapor state. By analyzing the Triticeae grains used, but also the milled material obtained at the respective stage, a person skilled in the art can readily determine the water content and readily ascertain the amounts of additional water which are required.

In the second milling stage, the endosperm fraction is further comminuted. In this case, fiber components can again be separated off in the manner described above. 2- to 4-stage methods are typical. The multistage character leads to higher purities of the individual fractions and to higher starch yield of the endosperm fraction. In this case the endosperm fraction is adjusted to the most favorable particle size for the liquefaction/saccharification. This step is frequently also termed fine milling. In fine milling, the endosperm fraction is generally milled to a median particle diameter in the range of 0.01 to 1.5 mm, and preferably to a particle size in the range from 0.025 to 1 mm, and especially in the range from 0.05 to 0.6 mm. The median particle diameter is mass-related and is preferably determined by means of sieve analysis in a manner known to those skilled in the art. In particular, it has proved to be advantageous when at least 80% by weight, in particular at least 90% by weight, and especially at least 95% by weight, of the particles have a diameter of not greater than 0.4 mm. In the case of a multistage fine milling procedure, preferably after each milling passage, separation into particles, the size of which is above the desired maximum size, proceeds, and particles, the size of which does not exceed the desired upper limit. Only the excessively large particles are then fed to a further milling passage.

Similarly, the bran fraction can be further comminuted for separating off the endosperm proportion adhering thereto, wherein separation into endosperm components and bran components is performed. The endosperm-rich fraction occurring in this process can be recirculated to the endosperm fraction of the first milling stage. Return preferably proceeds before or during the fine milling.

The fractions thus separated typically have the compositions given hereinbelow. The bran component typically has the following components in the following amounts (based on the total dry matter):

Crude protein: 8 to 18% by weight,
Starch: 8 to 20% by weight,
Crude fiber: 25 to 65% by weight,
Crude fat: 2 to 10% by weight,
Crude ash: 3 to 12% by weight.

The moisture content of the bran is typically between 5 and 20% by weight, preferably between 8 and 14% by weight.

The endosperm fraction typically has the following components in the following amounts (based on the total dry matter):

Crude protein: 3 to 30% by weight, preferably 5 to 15% by weight,
Starch: 50 to 90% by weight, preferably 55 to 85% by weight,
Crude fiber: 0.1 to 20% by weight, preferably 0.1 to 10% by weight, in particular 0.2 to 5% by weight, especially 0.3 to 2% by weight or 0.3 to 1.5% by weight,
Crude fat: 0.1 to 5% by weight, preferably 0.2 to 2% by weight,
Crude ash: 0 to 15% by weight, preferably 0.1 to 3% by weight.

The moisture content of the endosperm is typically between 5 and 20% by weight, preferably between 8 and 14% by weight.

Only the components relevant for feeds are reported for the bran and endosperm fractions, as are given by analysis typical therefor. In this case the value given for crude protein comprises total Kjeldahl nitrogen multiplied by the factor 6.25, that is to say in addition to proteins, e.g. other free amino acids, nucleic acids and also inorganic nitrogen are also included. The value given for crude fiber comprises, as main component, cellulose and hemicelluloses, but encrusting substances such as lignin are also detected. The value given for crude fat comprises all substances which, as do, e.g., triglycerides, free fatty acids and phospholipids, dissolve in fat solvents such as, e.g., light petroleum or hexane. The crude ash comprises all inorganic components which remain after heating to 550° C. over a relatively long time period. These are essentially minerals in the form of oxides and salts. In addition to the separately analyzed starch, non-starch polysaccharides such as, e.g., pentosans are not comprised, or comprised only imprecisely, by the analytical technique chosen.

The names crude protein, crude fiber components, crude fat and crude ash used here are familiar to those skilled in the art and are defined, for example, in Naumann, C., Bassler, R., 1976. VDLUFA-Methodenbuch, Band 3, Die chemische Untersuchung von Futtermitteln [German Association of Agricultural Analytical and Research Institutes (VDLUFA) Method Book, volume 3, Chemical analysis of feeds] (loose leaf collection with supplements of 1983, 1988, 1993, 1997 and 2004), VDLUFA-Verlag, Darmstadt, Germany [compilation of all parameters/methods relevant in Germany to the assessment of feeds].

Step b)

The resultant milled material, hereinafter also termed flour, which contains essentially the endosperm fraction and therefore the starch components, is then converted into an aqueous suspension.

According to a first embodiment of the invention, a procedure is followed such that the total amount of the milled material is mixed with an aqueous liquid, e.g. fresh water, recycled process water, e.g. from a subsequent fermentation or evaporation, or with a mixture of these liquids, wherein an aqueous suspension having a starch content of at least 30% by weight is obtained. This procedure is frequently also termed slurrying.

The amount of flour is preferably selected in such a manner that the suspension comprises 30 to 55% by weight, preferably 32 to 50% by weight, and very particularly preferably 35 to 45% by weight of starch, based on the total weight of the suspension (mash). Since 1 kg of starch generally yields >1.0 to 1.1 kg of mono-, di- and oligosaccharides in a liquefaction/saccharification, accordingly the total concentration of mono-, di-, and/or oligosaccharides in the resultant glucose after the saccharification is at least 320 g/kg, frequently in the range from >320 to 600 g/kg, preferably in the range from 330 to 500 g/kg, in particular in the range from 350 to 495 g/kg, and especially from 380 to 495 g/kg. In this case glucose generally makes up 80% by weight, in particular at least 90% by weight, based on the total amount of mono-, di- and/or oligosaccharides.

The temperature of the water used is generally selected in such a manner that the suspension has a temperature in the range from 30 to 53° C., preferably 40 to 50° C., and very particularly preferably 44 to 48° C. A temperature of 53° C. should preferably not be exceeded in order to prevent unwanted gelatinization of the starch.

The flour suspension can be produced discontinuously or continuously, wherein any auxiliaries for setting the pH, such as calcium hydroxide and/or sulfuric acid, and the liquefying enzyme required in step c) can be mixed with the aqueous liquid in advance or else can be added individually to the flour/water mixture. The sequence of addition is optional here. In the case of the discontinuous production of the flour suspension, all types of mixed reactors can be used. In the case of the continuous production, generally slow or rapid continuous mixers are used.

In this embodiment, the gluten is depleted subsequently to the saccharification in step c).

According to a second embodiment of the invention, the gluten is depleted before the saccharification. The depletion is generally effected only in a subquantity of the endosperm fraction used in step c), and so gluten is present in step c), and following step c) a further gluten depletion is carried out.

The gluten is generally depleted in a manner similar to the methods described at the outset, e.g. the batter method or the Martin method.

According to a preferred embodiment,
i) a subquantity of the endosperm fraction, typically 20 to 70%, in particular 30 to 60%, is converted into a dilute aqueous suspension of the endosperm fraction having a starch content of less than 30% by weight, typically 20 to <30% by weight, e.g. 20 to 28% by weight,
ii) the gluten components are depleted from this suspension, preferably up to a depletion degree of at least 70%, in particular at least 80%, and especially at least 90%, wherein a dilute aqueous suspension of the gluten-depleted endosperm fraction is obtained, and
iii) a further endosperm fraction is suspended in the aqueous suspension obtained in step ii), in such a manner that a starch content in the suspension of at least 30% by weight results.

In step i) generally a procedure is followed such that the desired subquantity is kneaded together with about 0.8 to 1.1 parts by weight of an aqueous liquid, e.g. fresh water, recycled process water, e.g. from a subsequent fermentation or evaporation, or with a mixture of these liquids, to form a dough. This dough comprises the starch and gluten components of the endosperm fraction. Optionally after a short standing phase, which can generally be 10 min to 1 h, the dough is suspended in an aqueous liquid as stated above. The amount of liquid is typically 1.7 to 3 parts by weight per one part by weight of the dough. The gluten component is generally substantially depleted or removed from the suspension by sieving. Optionally, fine sieving for removing fiber components can follow.

Alternatively, the desired subquantity can be kneaded together with about 0.4 to 0.6 part by weight of an aqueous liquid, e.g. fresh water, recycled process water, e.g. from a subsequent fermentation or evaporation, or with a mixture of these liquids, to form a dough. Optionally after a short standing phase, which can generally be 10 min to 1 h, the gluten-depleted starch fraction is washed out of the dough by treatment with an aqueous liquid as stated above and the action of mechanical energy, e.g. by kneading. Optionally, fine sieving for removing remainders of gluten and fiber components can follow.

In both cases a dilute gluten-depleted aqueous suspension of the endosperm fraction is obtained which generally has a starch content of less than 30% by weight, typically 20 to 30% by weight. This dilute suspension is subsequently mixed by adding the endosperm fraction (flour) obtained in step a), in such a manner that an aqueous suspension of the endosperm fraction results which has a starch content of at least 30% by weight. The amount of flour is preferably selected in such a manner that the suspension is 30 to 55% by weight, preferably 32 to 50% by weight, and very particularly preferably 35 to 45% by weight of starch, based on the total weight of the suspension.

The suspension in step iii) can be produced in a similar manner to production of the flour suspension of the $1^{st}$ embodiment, wherein any auxiliaries for setting the pH, such as calcium hydroxide and/or sulfuric acid, and the liquefying enzyme required in step c) can be mixed in advance with the dilute aqueous suspension or else can be added individually to the flour suspension. The sequence of addition is optional here.

Step c)

The suspension produced in step b) is then subjected to an enzymatic liquefaction and saccharification, wherein the starch components of the endosperm fraction are hydrolyzed to glucose. In a first step c.1), a liquefaction of the starch components in the suspension is carried out, wherein the starch components are typically digested or hydrolyzed to form sugar chains having 4 to 20, and in particular 8 to 12, glucose units. This step is hereinafter also called liquefaction.

The liquefaction can customarily proceed by adding enzymes. Methods therefor are known from the prior art cited at the outset, e.g. from "The Alcohol Textbook—A reference for the beverage, fuel and industrial alcohol industries", cited at the outset, chapter 2, pages 7 to 23.

For liquefying the starch proportion in the flour, in principle all starch-liquefying enzymes can be used, in particular α-amylases (enzyme class EC 3.2.1.1), for example α-amylases which are obtainable from *Bacillus lichenformis* or *Bacillus stearothennophilus*, inter alia those which are used for liquefying materials obtained by dry-milling methods in the context of bioethanol production. The α-amylases which are suitable for liquefaction are also commercially obtainable, for example from Novozymes under the name Termamyl 120 L, type L; or from Genencor under the name Spezyme. A combination of various α-amylases can also be used for liquefaction. The concentration of the enzyme in the mash, based on the starch content, is generally 0.01 to 0.4% by weight, preferably 0.02 to 0.3% by weight, frequently 0.03 to 0.2% by weight, and very particularly preferably 0.04 to 0.1% by weight.

Optionally, additionally a xylanase is further added. The xylanase is generally used in an amount of up to 2.0% by weight (based on the starch used), e.g. 0.01 to 2% by weight, frequently 0.02 to 1% by weight, preferably 0.05 to 0.5% by weight. Such enzymes which are commercially available, for example, under the name Shearzyme® 500 L (Novozymes A/S) reduce the viscosity of the starch suspension during the liquefaction and saccharification and the viscosity of the final glucose solution. In particular, when the method according to the invention is carried out industrially, frequently only small amounts of xylanase are necessary, and so the amount of xylanase used in such processes can be used in an amount of 0.02 to 0.5% by weight, and in particular 0.05 to 0.2% by weight, based on the starch used.

Advantageously, the amounts of starch-liquefying enzyme and flour are selected in such a manner that the viscosity during the gellation process is reduced sufficiently in order to enable effective mixing of the suspension, e.g. by means of agitators. Preferably, the viscosity of the reaction mixture during the gellation is a maximum of 20 Pas, particularly preferably a maximum of 15 Pas, and very particularly preferably a maximum of 8 Pas. The viscosity is measured generally using a Haake viscometer; Roto Visko RV20 type using the M5 measurement system and MVDIN measuring unit at a temperature of 50° C. and a shear rate of 200 s$^{-1}$.

Frequently, the liquefaction is carried out in the presence of at least one calcium salt. The calcium concentration in the mash is then set by adding a calcium salt to generally 10 to 200 ppm, preferably 15 to 100 ppm and very particularly preferably to 20 to 60 ppm. The presence of calcium ions, however, is not compulsory and a number of liquefying enzymes are known for the liquefaction and saccharification which deliver good conversion rates and yields also in the absence of calcium, and so in these cases the addition of calcium salts can be avoided.

For optimum activity of the starch-liquefying enzyme, the liquefaction is carried out preferably at least at times in the pH optimum of the liquefying enzyme, frequently at a pH in the slightly acidic range, generally in the range from 4.0 to 7.0, preferably in the range from 5.0 to 6.5, particularly preferably in the range from 5.3 to 6.0. Customarily, before or at the start of the liquefaction, pH adjustment is performed; this pH is generally monitored during the liquefaction and optionally adjusted. The pH is preferably adjusted using dilute mineral acids such as HCl, $HNO_3$, $H_2SO_4$ or $H_3PO_4$, with organic acids such as acetic acid, with alkali metal hydroxide such as NaOH or KOH, or alkaline earth metal hydroxide such as magnesium hydroxide or calcium hydroxide. Preferably, the pH is adjusted using calcium hydroxide and/or sulfuric acid.

For the liquefaction, the suspension produced in step b) is preferably heated to a temperature above the gelatinization temperature of the starch. Generally, a temperature in the range from 80 to 120° C., preferably from 90 to 115° C., and particularly preferably in the range from 95 to 110° C., is selected, wherein the temperature is preferably at least 5 K, in particular 10 K, and particularly preferably at least 20 K, e.g. 10 to 80 K, in particular 20 to 60 K, above the gelatinization temperature of the wheat starch). The liquefaction can also be carried out below the gelatinization temperature, e.g. using the enzymes or enzyme combinations described in WO 2004/113551.

In a preferred embodiment for liquefying the starch proportion, the mash is first heated to a temperature above the gelatinization temperature of the starch by introducing direct steam. Typically, heating is performed to a temperature which is at least 10 K, and in particular at least 20 K, e.g. 10 to 80 K, in particular 20 to 60 K, above the respective gelatinization temperature. Preferably, the suspension is heated to temperatures in the range from 80 to 120° C., in particular in the range from 90 to 115° C., and especially in the range from 95 to 110° C.

The direct steam used for heating is typically superheated steam which has a temperature of at least 105° C., in particular at least 110° C., e.g. 110 to 210° C. The use of saturated steam, however, is likewise possible. Preferably, the steam is introduced at superatmospheric pressure into the suspension. Accordingly the steam preferably has a pressure of at least 1.5 bar, e.g. 1.5 to 16 bar, in particular 2 to 12 bar.

Direct steam is introduced into the mash generally in such a manner that the steam is introduced into the suspension at an overpressure, preferably an overpressure of 1 to 10 or 11 bar, in particular 1.5 to 5 bar, and preferably at high velocity. Owing to the introduction of the steam, the suspension heats instantaneously to temperatures above 90° C., that is to temperatures above the gelatinization temperature.

Preferably, the heating with direct steam is performed in a continuous device into which the mash is fed continuously at a certain feed pressure which results from the viscosity of the suspension, the feed rate and the geometry of the device and into which the hot steam is fed at an overpressure, based on the feed pressure, via a controllable nozzle, in the region (or the zone) of the feed of the suspension. Owing to the feed of the steam at an overpressure, the suspension is not only heated, but mechanical energy is also introduced into the system which promotes further mixing of the flour particles, effects a particularly uniform energy input, and therefore causes a particularly uniform gelatinization of the granular starch particles in the flour. Typically, these devices have a tubular geometry. Preferably, the steam is introduced in the direction of the longitudinal axis of the tubular device. The suspension is generally fed at a shallow angle to the steam stream which generally does not exceed 50°. The controllable nozzle typically has a conical geometry which tapers in the direction of flow of the steam. In this nozzle is arranged a needle or a cone which is arranged on a rod which is displaceable in the longitudinal direction. Needle or cone, together with the cone of the nozzle, forms a gap. By displacing the needle or rod in the longitudinal direction, the size of the gap and thereby the cross-sectional area of the nozzle opening may be set in a simple manner, as a result of which the rate of steam introduction can be regulated in a simple manner.

Typically, these devices, in addition, have a mixing tube into which the suspension is transported after the steam introduction and is discharged from the device. This mixing tube is customarily arranged in the direction of the steam introduction. The mixing tube typically forms together with the nozzle a gap through which the suspension is transported. Via this gap, additional shear forces act during transport on the suspension and increase thereby the mechanical energy introduction into the suspension. The mixing tube can be arranged to be displaceable in the longitudinal direction. By displacing the mixing tube, the size of the gap opening may be adjusted in a simple manner and thereby the pressure drop in the device.

Such devices are known from the prior art under the name jet cookers, for example the device shown in "The Alcohol Textbook", chapter 2, loc. cit., FIG. 13, and are commercially available, for example under the name HYDCRUDE EATER® or JetCooker® from Hydro Thermal Corp. Waukesha, Wis., USA.

The mash heated by direct steam is generally subsequently thereto transferred into a post-reaction zone in order to continue the gelatinization of the starch components. At the same time the liquefying enzyme starts to hydrolyze the starch. In the post-reaction zone an overpressure typically prevails, typically an absolute pressure in the range from 2 to 8 bar. The temperatures in the post-reaction zone are typically in the range from 80 to 120° C., in particular in the range from 90 to 115° C. The residence time in this post-reaction zone can be, depending on the temperature of the suspension, in the range from 1 to 30 min, frequently 2 to 20 min, and in particular 5 to 10 min. The post-reaction zones typically have a tubular or columnar geometry. In one embodiment, the post-reaction zone has the geometry of a vertically arranged column. The suspension in this case, after it leaves the device for steam treatment, is applied in the upper region of the column and taken off in the lower region. In another embodiment of the invention, the post-reaction zone has a tubular geometry.

After it leaves the post-reaction zone, the suspension is generally cooled and a second liquefaction is then carried out. This cooling can proceed by expansion of the pressurized solution. Preferably the expansion is carried out as a flash evaporation in order to cool the suspension, preferably at temperatures of at most or below 110° C., in particular at most or below 105° C., e.g. in the range from 80 to 110° C., preferably 90 to 105° C., and very particularly preferably 95 to 100° C. Generally liquefaction of the thus disrupted starch then proceeds in a separate reaction vessel. Optionally it can be expedient, instead of adding the total amount of the liquefying enzyme before or during the heating, to add a subquantity thereof after setting the temperature for the second liquefaction. This subquantity can be 0 to 80%, preferably 10 to 60%, and very particularly preferably 15 to 40%, of the total amount of liquefying enzyme. The second liquefaction can proceed over a period of 30 to 240 min, preferably 45 to 180 min, and very particularly preferably 60 to 120 min. The second liquefaction can proceed in a continuous flow tube, continuously in a stirred-tank cascade, or in discontinuous stirred tanks. When stirred tanks are used it is advantageous to provide a sufficient number of stirred tanks which permits individual stirred tanks to be cleaned in parallel to the running operation without losing capacity.

For the complete breakdown of the starch to dextrins, the reaction mixture is kept at the set temperature, or optionally heated further, until the starch detection by iodine or optionally another test for detecting starch is negative or at least essentially negative. Optionally, in this case, one or more further subquantities of α-amylase, e.g. in the range from 0.001 to 0.5% by weight, and preferably 0.002 to 0.2% by weight, based on the total amount of the starch source used, can further be added to the reaction mixture.

Instead of heating the mash by direct steam, it can also be heated indirectly using a heating medium, e.g. steam, to the desired temperature in what are termed "wide gap" heat exchangers, which prevents dilution of the flour suspension by introduced steam. Here also, generally a post-reaction and a second liquefaction are carried out as described for the heating with direct steam. With regard to the measures taken here, the abovesaid applies in an analogous manner.

In this manner, an aqueous partial starch hydrolyzate is obtained which comprises the liquefied starch proportion from the flour, typically dextrins, and optionally further oligosaccharides and mono- or disaccharides, and also at least some of the protein components of the flour.

After liquefaction of the starch is completed, saccharification of the dextrins present in the aqueous partial starch hydrolyzate proceeds, i.e. their breakdown to glucose or sucrose. The saccharification can be carried out continuously or discontinuously in a manner known per se.

The dextrins (i.e. oligosaccharides) in the liquefied starch solution are generally saccharified enzymatically, i.e. using at least one enzyme saccharifying the dextrins. For this, in principle all glucoamylases (enzyme class EC 3.2.1.3) can be used, in particular glucoamylases which were obtained from *Aspergilus*, and especially those which are used for saccharifying materials obtained by dry milling methods in the context of producing bioethanol. The glucoamylases which are suitable for the saccharification are also commercially available, for example from Novozymes under the name Dextrozyme GA; or from Genencor under the name Optidex. A combination of various glucoamylases can also be used.

The at least one saccharifying enzyme, in particular at least one glucoamylase, is added to the dextrin-comprising liquid medium obtained after the liquefaction customarily in an amount of 0.001 to 5.0% by weight, preferably from 0.005 to 3.0% by weight, and particularly preferably from 0.01 to 2% by weight, especially 0.05 to 1.0% by weight, based on the total amount of the starch source used.

Generally, the liquefied starch solution is customarily cooled to, or brought to and held at the temperature optimum of the saccharifying enzyme or slightly thereunder, e.g. to 40 to 70° C., preferably 50 to 65° C., and in particular 60 to 63° C., and subsequently admixed with the saccharifying enzyme. Preferably, the aqueous partial starch hydrolyzate is subjected to a saccharification directly after the liquefaction. The hot aqueous partial starch hydrolyzate is then cooled to the abovementioned temperatures before the saccharifying enzyme is added. This cooling advantageously proceeds in a heat exchanger, wherein the energy which is being liberated can be utilized for preheating other process streams.

Advantageously, the saccharification proceeds at a pH in the optimum activity range of the enzyme used, preferably at a pH in the range from 3.0 to 5.5, in particular in the range from 4.0 to 5.0, and particularly preferably in the range from 4.2 to 4.8. Preferably, the pH is set to the desired value before addition of the saccharifying enzyme, in particular the glucoamylase.

The saccharification can proceed discontinuously in stirred reactors or continuously in a flow tube, or particularly preferably in a stirred-tank cascade. When stirred tanks are used it is advantageous to provide a sufficient number of stirred tanks which permits individual stirred tanks to be cleaned in parallel to the running operation without losing capacity.

After addition of the saccharifying enzyme, the dextrin-comprising suspension is preferably held at the temperature set for a period of e.g. 8 to 72 h or longer, if necessary, frequently 12 to 60 h, preferably 24 to 54 h, and particularly preferably 36 to 48 h, wherein the dextrins are saccharified to mono- and disaccharides. The progress of the saccharification can be followed by methods known to those skilled in the art, e.g. HPLC, enzyme tests or glucose test sticks. The saccharification is complete when the concentration of the monosaccharides no longer significantly increases or falls again.

Step d):

The saccharification produces an aqueous glucose solution which, in addition to glucose, optionally further comprises the unhydrolyzed components of the flour as solids in suspended form. These solids are primarily the gluten proportion of the endosperm fraction.

If the gluten was not already completely depleted before carrying out step c), according to the invention depletion of the gluten is carried out from the glucose following step c). It is also possible, and in many cases expedient, to carry out such a depletion not only before carrying out step c), but also subsequently thereto. In this case, in general, first a subquantity of the gluten from the starch material to be saccharified is depleted, for example by substantially or completely depleting the gluten component in a subquantity of the endosperm fraction, and uniting this subquantity which is depleted with respect to the gluten with the remainder of the endosperm fraction from step a) which is not depleted with respect to the gluten component, e.g. transferring it to a suspension and then carrying out step c) and step d).

For depletion of the gluten from the glucose, generally a procedure is followed such that the total amount of the gluten-comprising glucose solution produced in step c) is subjected to a solids separation. However, also only a substream of the gluten-comprising glucose solution produced in step b) can be subjected to a solids separation and the remaining gluten-comprising glucose fed to another use, for example bioethanol production.

Generally, depletion is carried out to an extent that at least 70% by weight, preferably at least 85% by weight, and in particular at least 90% by weight, or even at least 95% by weight of the gluten components comprised in the glucose solution are separated off.

The gluten and any bran optionally present can be separated off in any known liquid/solid separation, wherein mechanical methods such as centrifugation, decanting and filtration are preferred, including combinations of these measures.

For separating off the solids from the glucose solution, it has proved to be advantageous when the glucose solution which is fed to the separation has a temperature in the range from 60 to 100° C., in particular in the range from 70 to 90° C., and particularly preferably in the range from 75 to 85° C. For this, the glucose solution obtained in step b) is generally heated to the desired temperature before depletion of the solids components gluten and bran. The heating advantageously proceeds in a heat exchanger, wherein the energy required can be utilized for cooling other process streams.

In addition, it has proved to be advantageous when the pH of the glucose solution is set, before depletion of the solids, in the range from 4.0 to 6.5, in particular in the range from 4.5 to 6.0 and particularly preferably in the range from 5.0 to 5.5. For adjusting the pH, any optional base, but preferably an alkali metal hydroxide, e.g. sodium hydroxide solution, or ammonia, can be used.

The depletion produces a low-solids glucose solution and a solids-rich fraction which comprises the gluten and optionally bran components and which has a lower glucose proportion than the low-solids glucose solution.

The low-solids glucose solution can still comprise small amounts of undissolved solids, wherein the amount does not exceed generally 15% by volume, in particular 10% by volume, and especially 5% by weight, based on the total volume of the aqueous glucose solution, and is frequently in the range from 0.001 to 15% by volume, in particular in the range from 0.01 to 10% by volume, and particularly preferably in the range from 0.02 to 5% by volume, based on the total volume of the aqueous glucose solution. The undissolved solids are determined by centrifugation of the glucose solution in graduated centrifuge tubes at 1650 g over 15 min and subsequently reading off the amount of undissolved solids.

For achieving a high glucose yield it is advantageous if the solids-rich fraction obtained in the solid/liquid separation is resuspended in water and then subjected to a repeated solid/liquid separation. The amount of water is typically in the range from 1 to 15 l/kg of suspended solids, calculated as dry matter, or in the range from 1 to 20 l per 1 of moist separated solids. This second solid/liquid separation produces a liquid phase which comprises parts of the glucose in dissolved form contained in the solids phase of the first solid/liquid separation. The liquid phase is then added to the liquid phase of the first solid/liquid separation. For a further increase of the glucose yield this process, i.e. the resuspension of the solid obtained in water and subsequent solid/liquid separation can be repeated once or several times, wherein in each case the aqueous glucose solutions obtained are added to the glucose solution obtained in the first solid/liquid separation.

The temperature at which the second and optionally other solid/liquid separation(s) are carried out is typically in the range from 60 to 100° C., preferably in the range from 70 to 90° C., and particularly preferably in the range from 75 to 85° C. Regarding the pH, that stated above for the first solid/liquid separation applies.

The water which is used for resuspending the solids-rich fraction of the first and other solid/liquid separations can be fresh water. However, frequently, for resuspending the aqueous glucose solution of a later solid/liquid separation is used in order to reduce the dilution of the combined low-solids glucose solutions of the individual solid/liquid separation stages by fresh water and decrease the fresh water requirement overall. For example, in three successive solid/liquid separations the liquid phase of the third solid/liquid separation is used for resuspending the solids phase of the second solid/liquid separation, and the liquid phase of the second solid/liquid separation is used for resuspending the solids-rich phase of the first solid/liquid separation. In addition to fresh water, alternatively process water can also be used which occurs, e.g. as condensate, in the later concentration by evaporation of the glucose solution, or occurs in the drying of the by-products (e.g. gluten or biomass).

For a further decrease in the solids proportions in the aqueous glucose solutions thus obtained, it can be advantageous to subject these to what is called a polishing stage in order to deplete other solids present therein. The further depletion can be carried out by any known type of solid/liquid separation, such as, for example, membrane filtration, including microfiltration and ultrafiltration, conventional filtration, flotation, centrifugation, decanting or separating. Multistage embodiments which result from any desired interconnection of the methods mentioned here are also conceivable.

The low-solids glucose solution which is obtainable after depletion of the gluten and optionally of the bran present from the aqueous glucose obtained in step b) is novel and is suitable particularly for producing chemicals. The aqueous glucose solution is therefore likewise subject matter of the present application.

The dry matter proportion or dry matter content is taken to mean the total amount of dissolved and undissolved solids in the aqueous glucose solution. These may be determined by evaporating the glucose solution in a manner known per se. For this a defined amount of the respective glucose solution is evaporated to dryness in the drying cabinet at 80° C. Weighing the dry residue gives the dry matter content. Alternatively, drying trolleys can be used, as are marketed for this purpose, for example by PCE Deutschland, Meschede.

Based on the solids present in the aqueous glucose solution, i.e. the dry matter content, the aqueous glucose solution has the following characteristic components:

a) 80 to 98% by weight, preferably 93 to 97% by weight of sugar in the form of glucose and optionally disaccharides, such as sucrose, maltose and isomaltose,
b) 0.5 to 7.0% by weight, preferably 1.0 to 4.0% by weight of crude protein,
c) 0.01% by weight to 0.1% by weight of crude fiber,
d) 80 to 1000 mg/kg, (0.008 to 0.1% by weight), preferably 100 to 800 mg/kg of free amino acids and
e) 0.01 to 1.0% by weight of crude ash components.

A glucose solution having such a composition is novel and is likewise subject matter of the present invention.

In addition, the glucose solution can still comprise small amounts of oil/fat from the germ. The majority of any oil/fat components, however, is generally separated off together with the gluten in step d). The same applies to any bran components which are not separated off before carrying out step c).

The invention further relates to the gluten occurring in step d) of the method according to the invention. In the method according to the invention it occurs in an amount of 4 to 40% by weight, in particular 8 to 30% by weight, based on the dry matter of the grain used. The gluten generally has the following gross composition, wherein the figures are in each case based on the total dry matter of the gluten.

a) 10 to 60% by weight, in particular 20 to 55% by weight, of crude protein;
b) 1 to 65% by weight, in particular 2 to 60% by weight, of sugar components;
c) up to 20% by weight, frequently 0.5 to 10% by weight, of crude fat, vegetable fats and/or vegetable oils;
d) up to 20% by weight, in particular 1 to 12% by weight, of crude fiber components; and
e) up to 15% by weight, e.g. 0.1 to 10% by weight, of solid components different therefrom, also called crude ash.

The gluten separated off in step d) is a finely divided solid which, after separation, generally has a moisture content in the range from 50 to 85% by weight, and in particular in the range from 55 to 75% by weight, based on the total mass of the gluten separated off. The gluten can be dried in a manner known per se to give a finely divided, non-dust-forming to slightly dust-forming and non-sticky powder. The moisture content is then typically less than 50% by weight, generally less than 30% by weight, especially less than 15% by weight. A moist gluten having a dry matter proportion of 35% by weight, or a water content of 185%, based on the dry gluten, behaves like a solid.

The median particle size of the gluten particles (weighed mean, determined by light scattering or by sieve analysis) is typically in the range from 50 to 600 μm, and in particular in the range from 100 to 500 μm.

The gluten according to the invention has a high water absorption capacity and is able to absorb up to 185% by weight of water, based on its own dry weight, without becoming sticky. It is therefore particularly suitable as a formulation aid, in particular for producing solid formulations of moist or pasty substances which themselves have a tendency to stick together. In particular, the gluten according to the invention is suitable for formulating a biomass as occurs in a fermentation. In this manner a non-sticky product comprising biomass and gluten is obtained which can be used, for example, as feed or feed component.

The gluten according to the invention is additionally distinguished by a high absorption capacity for oils and oily substances, in particular for vegetable oils. It is therefore particularly suitable for producing solid formulations of high-value vegetable oils or vegetable oil components, or substances having properties comparable to tocopherols.

By hydrolysis of the proteins present in the gluten according to the invention, soluble peptides can be produced which, optionally after separating off the non-hydrolyzed gluten components, can be used, for example, in human nutrition. The hydrolysis can be carried out, e.g. enzymatically, by corresponding proteases. For separating off the non-hydrolyzed protein components, customary methods of solid/liquid separation can be used such as, e.g., centrifugation or filtration methods, in the special membrane filtration method.

The aqueous glucose obtained after the solid/liquid separation(s) can optionally be concentrated to the desired glucose concentration in a single-stage or multistage concentration by evaporation. For this the aqueous glucose solution is concentrated at temperatures in the range from 50 to 100° C., preferably in the range from 70 to 95° C., and particularly preferably in the range from 80 to 90° C., preferably under reduced pressure. Preferably, the concentration is operated until a glucose concentration of at least 40% by weight, in particular at least 50% by weight, particularly preferably at least 55% by weight, and very particularly preferably at least 60% by weight, for example in the range from 40 to 80% by weight, preferably in the range from 50 to 75% by weight, particularly preferably in the range from 55 to 70% by weight and very particularly preferably in the range from 60 to 65% by weight, is achieved.

Use of the Glucose for Producing Organic Substances

The glucose solution thus obtained can subsequently be used as carbon source for producing organic substances, i.e. chemicals.

The expression chemicals must be interpreted broadly and comprises all organic substances, i.e. not only defined low-molecular-weight compounds, oligomers, polymers, including enzymes, but also biomasses having characteristic properties such as, e.g., yeasts or single cell proteins which are produced or can be produced starting from glucose. The production of organic matter can be performed not only by fermentation but also by ways not involving fermentation. The method according to the invention offers, in particular, advantages in the production of chemicals which are different from ethanol, since here generally greater demands are made of the glucose quality.

Examples of organic substances which are producible from glucose by pathways not involving fermentation comprise 5-hydroxymethylfurfural, laevulinic acid, gluconic acid, glucuronic acid, 2-ketogluconic acid, glutaric acid, sorbitol, isosorbide and alkylpolyglucosides, polyols such as ethylene glycol, propylene glycol and high fructose corn syrup (HFCS).

Examples of organic substances which are producible from glucose by pathways involving fermentation are, for example, optionally hydroxyl-bearing mono-, di- and tricarboxylic acids having 2 to 10 carbon atoms, e.g. tartaric acid, itaconic acid, succinic acid, acetic acid, propionic acid, lactic acid, 3-hydroxypropionic acid, fumaric acid, maleic acid, 2,5-furandicarboxylic acid, glutaric acid, laevulinic acid, gluconic acid, aconitic acid and diaminopimelic acid and citric acid;

proteinogenic and non-proteinogenic amino acids, e.g. lysine, glutamate, methionine, phenylalanine, aspartic acid, tryptophan and threonine;

purine bases and pyrimidine bases;

nucleosides and nucleotides, e.g. nicotinamide adenine dinucleotide (NAD) and adenosine 5'-monophosphate (AMP);

lipids, saturated and unsaturated fatty acids preferably having 10 to 22 carbon atoms, e.g. γ-linolenic acid, dihomo-γ-linolenic acid, arachidonic acid, eicosapentaenoic acid and docosahexaenoic acid;

diols having 3 to 10 carbon atoms, e.g. propanediol and butanediol;

polyhydric alcohols having 3 or more hydroxyl groups, e.g. having 3, 4, 5 or 6 OH groups, e.g. glycerol, sorbitol, manitol, xylitol and arabinitol;

long-chain alcohols having at least 4 carbon atoms, e.g. having 4 to 22 carbon atoms, e.g. butanol;

carbohydrates, e.g. hyaluronic acid and trehalose;

aliphatic amines, in particular aliphatic diamines having 3 to 10 carbon atoms such as 1,5-pentanediamine;

aromatic compounds, e.g. aromatic amines, vanillin and indigo;

vitamins and provitamins, e.g. ascorbic acid, vitamin $B_6$, vitamin $B_{12}$ and riboflavin;

cofactors and nutraceuticals;

proteins, e.g. enzymes such as amylases, pectinases, acid, hybrid or neutral cellulases, esterases such as lipases, pancreases, proteases, xylanases and oxidoreductases such as laccase, catalase and peroxidase, glucanases, and phytases;

yeasts, e.g. baker's yeasts and brewer's yeasts;

carotenoids, e.g. lycopene, β-carotene, astaxanthin, zeaxanthin and canthaxanthin;

ketones having 3 to 10 carbon atoms, e.g. acetone and acetoin;

lactones, e.g. γ-butyrolactone;

polyhydroxyalkanoates, e.g. polyhydroxyacetate;

polylactides;

polysaccharides, e.g. glucan, mannan, galactan;

polyisoprenoids;

polyamides and cyclodextrins.

The expression "cofactor" comprises non-proteinaceous compounds which are necessary for the appearance of a usual enzyme activity. These compounds can be organic or inorganic; the cofactor molecules according to the invention are preferably organic. Examples of such molecules are NAD and nicotinamide adenine dinucleotide phosphate (NADP); the precursor of these cofactors is niacin.

The expression "nutraceutical" comprises food additives which are health-promoting in the case of plants and animals, in particular humans. Examples of such molecules are vitamins, antioxidants and certain lipids, e.g. polyunsaturated fatty acids.

Use of Glucose in a Fermentation

The invention preferably relates to the use of the glucose solution obtainable according to the invention as a glucose source for the production by fermentation of an organic substance as defined above.

Accordingly, the invention further relates to a method for producing an organic substance by fermentation, which comprises the following steps:

i. providing an aqueous glucose solution according to the invention, e.g. by producing the glucose solution according to the method according to the invention and ii. adding the glucose solution to a fermentation medium which comprises a microorganism which is capable of overproduction of the organic substance.

The fermentation can be carried out in any customary manner known to those skilled in the art. For this, the microorganism respectively desired is generally cultured using an aqueous glucose produced according to the invention.

The fermentation method can be operated not only discontinuously (batchwise), but also semicontinuously (fed-batch procedure, including fed batch with intermediate harvesting), wherein the semicontinuous procedure is preferred.

For example, the aqueous glucose solution obtained by the method according to the invention (also referred to below as glucose according to the invention)—optionally together with a conventional sugar source, and optionally after dilution with water and addition of customary media components such as buffer, nutrient salts, nitrogen sources such as ammonium sulfate, urea etc., complex nutrient media components, comprising amino acids such as yeast extracts, peptone, CSL and the like, is inoculated with the desired microorganism and these can be multiplied under fermentation conditions until the microorganism concentration has reached the steady state desired for the fermentation. In this case the sugar present in the glucose solution according to the invention is metabolized and the desired product of value formed (what is termed batch procedure or batch phase).

Conventional sugar source in the context of this invention means basically all metabolizable mono-, di- and/or oligosaccharides which are not obtained by the method according to the invention. These include both the pure form mono-, di- and/or oligosaccharides and mixtures thereof and compositions which comprise metabolizable mono-, di- and/or oligosaccharides at a concentration of at least 45% by weight and which are typically essentially free of water-insoluble solids, e.g. a low quality molasses having 45 and 50% by weight of sugar.

Owing to the high proportion of free amino acids in the glucose according to the invention, surprisingly the addition of other complex nutrient media components can be dispensed, or its amount drastically reduced, which is a further advantage of the glucose solution according to the invention.

In the fed-batch procedure, the fermentation process is further continued by adding the glucose solution obtainable according to the invention. In this case the metabolic product overproduced by the microorganism accumulates in the fermentation broth, wherein the metabolic product can be present not only in the cells of the microorganism but also in the aqueous phase of the fermentation medium.

Preferably, the fermentation is carried out semicontinuously, i.e. as fed-batch process. In this case a procedure is followed such that the microorganism is first multiplied using a glucose solution according to the invention and/or another sugar source, until the desired microorganism concentration in the fermenter is achieved. The aqueous glucose solution according to the invention, optionally with one or more other conventional sugar sources, is then fed to the fermenter. This maintains the fermentation process and the metabolic product overproduced by the microorganism accumulates in the fermentation broth (see above). The sugar content can be regulated in the fermentation broth, in particular via the feed rate of the aqueous glucose according to the invention. Generally, the feed rate is adjusted such that the glucose concentration in the fermentation broth is in the range from >0% by weight to about 5% by weight and in particular does not exceed a value of 3% by weight.

The glucose according to the invention can optionally be sterilized before the fermentation, wherein the contaminating microorganisms are customarily thermally killed. For this the glucose according to the invention is customarily heated to temperatures above 80° C. The killing or lysis of the contaminants can proceed immediately before the fermentation. For this the entire sugar-comprising liquid medium is fed to the sterilization.

The invention relates in particular to a method for producing organic compounds which are different to bioethanol, in particular organic, preferably nonvolatile compounds having at least 3 carbon atoms or having at least 2 carbon atoms and at least 1 nitrogen atom. These compounds by nature have hydrogen and optionally oxygen and optionally phosphorus and/or sulfur as further atoms. In this case nonvolatile organic compounds are taken to mean those compounds which cannot be obtained from the fermentation broth undecomposed by means of distillation.

These compounds generally have a boiling point above the boiling point of water, frequently above 150° C., and in particular above 200° C. at atmospheric pressure. Generally these are compounds which are present in the solid state under standard conditions (298 K, 101.3 kPa). However, it is also possible to use the sugar-comprising liquid medium according to the invention in a fermentation for producing nonvolatile metabolic products which have, at atmospheric pressure, a melting point below the boiling point of water or/and an oily consistency.

In particular, the method according to the invention is suitable for producing enzymes, amino acids, vitamins, nucleotides, di-, oligo- and polysaccharides, aliphatic monoand dicarboxylic acids having 3 to 10 carbon atoms, aliphatic hydroxycarboxylic acids having 3 to 10 carbon atoms, ketones having 3 to 10 carbon atoms, alkanols having 4 to 10 carbon atoms and alkanediols having 3 to 10 carbon atoms, and in particular 3 to 8 carbon atoms, and amines, in particular aliphatic diamines having 3 to 10 carbon atoms.

It is obvious to those skilled in the art that the compounds produced by fermentation in such a manner are obtained in each case in the enantiomeric form produced by the microorganisms used (if different enantiomers exist). For instance, e.g., the amino acids are generally obtained as the respective L enantiomer.

The microorganisms used in the fermentation are directed in a manner known per se toward the respective metabolic products as described in detail hereinafter. They can be of natural origin or be genetically modified. Examples of suitable microorganisms and fermentation methods are given, e.g. in Table A.

TABLE A

| Substance | Microorganism | Reference |
|---|---|---|
| Tartaric acid | Lactobacilli, (e.g. Lactobacillus delbrueckii) | Rehm, H.-J.: Biotechnology, Weinheim, VCH, 1980 and 1993-1995; Gutcho, Chemicals by Fermentation, Noyes Data Corporation (1973), |
| Itaconic acid | Aspergillus terreus, Aspergillus itaconicus | Jakubowska, in Smith and Pateman (editors), Genetics and Physiology of Aspergillus, London: Academic Press 1977; Miall, in Rose (editors), Economic Microbiology, Vol. 2, pp. 47-119, London: Academic Press 1978; U.S. Pat. No. 3,044,941 (1962). |
| Succinic acid | Actinobacillus sp. 130Z, Anaerobiospirillum succiniproducens, Actinobacillus succinogenes, E. coli | Int. J. Syst. Bacteriol. 26, 498-504 (1976); EP 249773 (1987), inventors: Lemme and Datta; U.S. Pat. No. 5,504,004 (1996), inventors: Guettler, Jain and Soni; Arch. Microbiol. 167, 332-342 (1997); Guettler MV, Rumler D, Jain MK., Actinobacillus succinogenes sp. nov., a novel succinic-acid-producing strain from the bovine rumen. Int J Syst Bacteriol. 1999 Jan; 49 Pt 1: 207-16; U.S. Pat. No. 5,723,322, U.S. Pat. No. 5,573,931, U.S. Pat. No. 5,521,075, WO99/06532, U.S. Pat. No. 5,869,301, U.S. Pat. No. 5,770,435 |
| Hydroxypropionic acid | Lactobacillus delbrückii, L. leichmannii or Sporolactobacillus inulinus | RÖMPP Online Version 2.2 |
| Propionic acid | Propionibacterium, e.g. P. arabinosum, P. schermanii, P. freudenreichii, Clostridium propionicum, | Rehm, H.-J.: Biotechnology, Weinheim, VCH, 1980 and 1993-1995; Gutcho, Chemicals by Fermentation, Noyes Data Corporation (1973), |
| Diaminopimelic acid | Corynebacterium glutamicum | Rehm, H.-J.: Biotechnology, Weinheim, VCH, 1980 and 1993-1995; Gutcho, Chemicals by Fermentation, Noyes Data Corporation (1973), |
| Citric acid | Aspergillus niger, Aspergillus wentii | Crit. Rev. Biotechnol. 3, 331-373 (1986); Food Biotechnol. 7, 221-234 (1993); 10, 13-27 (1996). |
| Aconitic acid | Aspergillus niger, Aspergillus wentii | Crit. Rev. Biotechnol. 3, 331-373 (1986); Food Biotechnol. 7, 221-234 (1993); 10, 13-27 (1996).; Rehm, H.-J.: Biotechnology, Weinheim, VCH, 1980 and 1993-1995; |
| Malic acid | Aspergilli, e.g. Aspergillus flavus, A. niger, A. oryzae, Corynebacterium | U.S. Pat. No. 3,063,910 |
| Gluconic acid | Aspergilli, e.g. A. niger | Gutcho, Chemicals by Fermentation, Noyes Data Corporation (1973), |
| Butyric acid | Clostridium (e.g. Clostridium acetobutylicum, C. butyricum) | Rehm, H.-J.: Biotechnology, Weinheim, VCH, 1980 and 1993-1995; |
| Lactic acid | Lactobacillus, e.g. L. delbrückii, L. leichmannii, | Rehm, H.-J.: Biotechnology, Weinheim, VCH, 1980 and 1993-1995; |
| Lysine | Corynebacterium glutamicum | Ikeda, M.: Amino Acid Production Process (2003), Adv. Biochem. Engin/Biotechnol 79, 1-35. |
| Glutamate | Corynebacterium glutamicum | Ikeda, M.: Amino Acid Production Process (2003), Adv. Biochem. Engin/Biotechnol 79, 1-35. |
| Methionine | Corynebacterium glutamicum | Ikeda, M.: Amino Acid Production Process (2003), Adv. Biochem. Engin/Biotechnol 79, 1-35. |
| Phenylalanine | Corynebacterium glutamicum, E. coli | Trends Biotechnol. 3, 64-68 (1985); J. Ferment. Bioeng. 70, 253-260 (1990). |
| Threonine | E. coli | Ikeda, M.: Amino Acid Production Process (2003), Adv. Biochem. Engin/Biotechnol 79, 1-35. |
| Aspartic acid | E. coli | Ikeda, M.: Amino Acid Production Process (2003), Adv. Biochem. Engin/Biotechnol 79, 1-35 + literature cited therein, |

TABLE A-continued

| Substance | Microorganism | Reference |
|---|---|---|
| Purine and pyrimidine bases | *Bacillus subtilis* | Gutcho, Chemicals by Fermentation, Noyes Data Corporation (1973)<br>Rehm, H.-J.: Biotechnology, Weinheim, VCH, 1980 and 1993-1995;<br>Gutcho, Chemicals by Fermentation, Noyes Data Corporation (1973), |
| Nicotinamide adenine dinucleotide (NAD) | *Bacillus subtilis* | Rehm, H.-J.: Biotechnology, Weinheim, VCH, 1980 and 1993-1995;<br>Gutcho, Chemicals by Fermentation, Noyes Data Corporation (1973), |
| Adenosine 5'-monophosphate (AMP) | *Bacillus subtilis* | Rehm, H.-J.: Biotechnology, Weinheim, VCH, 1980 and 1993-1995;<br>Gutcho, Chemicals by Fermentation, Noyes Data Corporation (1973), |
| γ-Linolenic acid | *Mucor, Mortiella, Aspergillus* spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by Pythium irregulare for Lipid Production. Master Thesis Lousiana State University, Oct. 31, 2002 (URN etd-1111102-205855). |
| Dihomo-γ-linolenic acid | *Mortiella, Conidiobolus, Saprolegnia* spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by Pythium irregulare for Lipid Production. Master Thesis Lousiana State University, Oct. 31, 2002 (URN etd-1111102-205855). |
| Arachidonic acid | *Mortiella, Phytium* spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by Pythium irregulare for Lipid Production. Master Thesis Lousiana State University, Oct. 31, 2002 (URN etd-1111102-205855). |
| Eicosapentaenoic acid | *Mortiella, Phytium* spp., *Rhodopseudomonas, Shewanella* spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by *Pythium irregulare* for Lipid Production. Master Thesis Lousiana State University, Oct. 31, 2002 (URN etd-1111102-205855). |
| Docosahexaenoic acid | *Thraustochytrium, Entomophthora* spp., *Rhodopseudomonas, Shewanella* spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by Pythium irregulare for Lipid Production. Master Thesis Lousiana State University, Oct. 31, 2002 (URN etd-1111102-205855). |
| Propanediol | *E. coli* | DE 3924423, US 440379, WO 9635799, U.S. Pat. No. 5,164,309 |
| Butanediol | *Enterobacter aerogenes, Bacillus subtilis, Klebsiella oxytoca* | Rehm, H.-J.: Biotechnology, Weinheim, VCH, 1980 and 1993-1995;<br>Gutcho, Chemicals by Fermentation, Noyes Data Corporation (1973);<br>H. G. SCHLEGEL and H. W. JANNASCH, 1981;<br>Afschar et al.: Microbial production of 2,3-butanediol. CIT 64 (6), 2004, 570-571 |
| Butanol | *Clostridium* (e.g. *Clostridium acetobutylicum, C. propionicum*) | Rehm, H.-J.: Biotechnology, Weinheim, VCH, 1980 and 1993-1995;<br>Gutcho, Chemicals by Fermentation, Noyes Data Corporation (1973), |
| Glycerol | Yeast, *Saccharomyces rouxii* | Gutcho, Chemicals by Fermentation, Noyes Data Corporation (1973), |
| Mannitol | *Aspergillus candida, Torulopsis mannitofaciens* | Gutcho, Chemicals by Fermentation, Noyes Data Corporation (1973), |
| Arabitol | *Saccharomyces rouxii, S. mellis, Sclerotium glucanicum, Pichia ohmeri* | Gutcho, Chemicals by Fermentation, Noyes Data Corporation (1973), |
| Xylitol | *Saccharomyces cerevisiae* | Gutcho, Chemicals by Fermentation, Noyes Data Corporation (1973), |
| Hyaluronic acid | *Streptococcus* sp. | Rehm, H.-J.: Biotechnology, Weinheim, VCH, 1980 and 1993-1995; |
| Trehalose | *Brevibacterium, Corynebacterium, Microbacterium, Arthrobacter* spp., *Pleurotus* genus, *Filobasidium floriforme* | JP 05099974, JP 06311891, FR 2671099, EP 0555540, JP 3053791, Miyazaki, J.-I., Miyagawa, K.-I., Sugiyama, Y.: Trehalose Accumulation by Basidiomycotinous Yeast, *Filobasidium floriforme*. Journal of Fermentation and Bioengineering 81, (1996) 4, 315-319. |
| Ascorbic acid | *Gluconobacter melanogenes* | RÖMPP Online Version 2.2 |

TABLE A-continued

| Substance | Microorganism | Reference |
|---|---|---|
| Vitamin $B_{12}$ | *Propionibacterium* spp., *Pseudomonas denitrificans* | Chem. Ber. 1994, 923-927; RÖMPP Online Version 2.2 |
| Riboflavin | *Bacillus subtilis*, *Ashbya gossypii* | WO 01/011052, DE 19840709, WO 98/29539, EP 1186664; Fujioka, K.: New biotechnology for riboflavin (vitamin $B_2$) and character of this riboflavin. Fragrance Journal (2003), 31(3), 44-48. |
| Vitamin $B_6$ | *Rhizobium tropici*, *R. meliloti* | EP0765939 |
| Enzymes | Apergilli (e.g. *Aspergillus niger A. oryzae*), *Trichoderma*, *E. coli*, *Hansenula* or *Pichia* (e.g. *Pichia pastorius*), *Bacillus* (e.g. *Bacillus licheniformis*, *B. subtilis*) and many others | Rehm, H.-J.: Biotechnology, Weinheim, VCH, 1980 and 1993-1995; Gutcho, Chemicals by Fermentation, Noyes Data Corporation (1973), |
| Zeaxanthin | *Dunaliella salina* | Jin et al (2003) Biotech. Bioeng. 81: 115-124 |
| Canthaxanthin | *Brevibacterium* | Nelis et al (1991) J Appl Bacteriol 70: 181-191 |
| Lycopene | *Blakeslea trispora*, *Candida utilis* | WO 03/056028, EP 01/201762, WO 01/12832, WO 00/77234, Miura et al (1998) Appl Environ Microbiol 64: 1226-1229 |
| β-Carotene | *Blakeslea trispora*, *Candida utilis* | Kim S., Seo W., Park Y., Enhanced production of beta-carotene from *Blakeslea trispora* with Span 20, Biotechnology Letters, Vol 19, No 6, 1997, 561-562; Mantouridou F., Roukas T.: Effect of the aeration rate and agitation speed on beta-carotene production and morphology of *Blakeslea trispora* in a stirred tank reactor: mathematical modelling, Biochemical Engineering Journal 10 (2002), 123-135; WO 93/20183; WO 98/03480, Miura et al (1998) Appl Environ Microbiol 64: 1226-1229 |
| Astaxanthin | *Phaffia rhodozyma*; *Candida utilis* | U.S. Pat. No. 5,599,711; WO 91/02060, Miura et al (1998) Appl Environ Microbiol 64: 1226-1229 |
| Polyhydroxy-alkanoates, polyesters | *Escherchia coli*, *Alcaligenes latus*, and many others | S. Y. Lee, Plastic Bacteria, Progress and Prospects for polyhydroxyalkanoate production in bacteria, Tibtech, vol. 14, (1996), pp. 431-438., Steinbüchel, 2003; Steinbüchel (editor), Biopolymers, 1$^{st}$ edition, 2003, Wiley-VCH, Weinheim and literature cited there |
| Polysaccharides | *Leuconostoc mesenteroides*, *L. dextranicum*, *Xanthomonas campestris*, and many others | Rehm, H.-J.: Biotechnology, Weinheim, VCH, 1980 and 1993-1995; Gutcho, Chemicals by Fermentation, Noyes Data Corporation (1973), |
| Polyisoprenoids | *Lactarius* sp., *Hygrophorus* sp., *Russula* sp. | Steinbüchel (editor), Biopolymers, 1$^{st}$ edition, 2003, Wiley-VCH, Weinheim and literature cited there |
| Acetone | *Clostridium* (e.g. *Clostridium acetobutylicum*, *C. propionicum*) | Rehm, H.-J.: Biotechnology, Weinheim, VCH, 1980 and 1993-1995; Gutcho, Chemicals by Fermentation, Noyes Data Corporation (1973) |
| Acetoin | *Enterobacter aerogenes*, *Clostridium acetobutylicum*, *Lactococcus lactis* | Lengeler, J. W., Drews, G., Schlegel, H. G.: editors, Biology of the Procaryotes, Thieme, Stuttgart (1999), p.307; RÖMPP Online-Edition |
| Vanillin | *Pseudomonas putida*, *Amycolatopsis* sp. | Priefert, H., Rabenhorst, J., Seinbüchel, A. Biotechnological production of vanillin. Appl. Microbiol. Biotechnol. 56, 296-314 (2001) |
| Thuringensin | *Bacillus thuringiensis* | Jian-Zhong Jong et al.: Fed-batch culture of *Bacillus thuringiensis* for thuringensin production in a tower type bioreactor. Biotechnology and Bioengineering 48 (3) (2004), 207-213. |
| Polyketides | *Streptomyces fradiae*, *Sorangium cellulosum* | Kirst: Fermentation-derived compounds as a source for new products. Pure & Appl. Chem. 70 (2), (1998), 335-338; Zirkle et al.: Heterologous production of the antifungal polyketide antibiotic soraphen A of *Sorangium* cellulosum So ce26 in Streptomyces lividans. Microbiology 150 (8), (2004), 2761-74. |
| Gibberellic acid | *Gibberella fujikuroi* | Hollmann et al.: Extraktiv-Fermentation von Gibberellinsäure mit *Gibberella fujikuroi* [Extractive fermentation of gibberellic acid with *Gibberella fujikuroi*]. CIT 7 (1995), 892-895. |
| Indigo | *Escherichia coli* JB 102 | Berry, A., Dodge, T. C., Pepsin, M., Weyler, W.: Application of metabolic engineering to improve both the production and use of biotech indigo. Journal of Industrial Microbiology & Biotechnology 28 (2002), 127-133. |

In preferred embodiments of the invention, the organic compound produced is selected from optionally hydroxyl-bearing mono-, di- and tricarboxylic acids having 3 to 10 carbon atoms, proteinogenic and non-proteinogenic amino acids, purine bases, pyrimidine bases; nucleosides, nucleotides, lipids; saturated and unsaturated fatty acids; diols having 4 to 10 carbon atoms, polyhydric alcohols having 3 or more hydroxyl groups, long-chain alcohols having at least 4 carbon atoms, carbohydrates, in particular di-, oligo- and polysaccharides, aromatic compounds, vitamins, provitamins, cofactors, nutraceuticals, proteins, carotenoids, ketones having 3 to 10 carbon atoms, lactones, amines, biopolymers and cyclodextrins.

A first preferred embodiment of the invention relates to the use of the aqueous glucose solution obtainable according to the invention in a production by fermentation of enzymes, e.g. the abovementioned enzymes such as phytases, xylanases or glucanases.

A second preferred embodiment of the invention relates to the use of the aqueous glucose solution obtainable according to the invention in a production by fermentation of amino acids, e.g. the abovementioned amino acids such as lysine, methionine, threonine or glutamate.

A further preferred embodiment of the invention relates to the use of the aqueous glucose solution obtainable according to the invention in a production by fermentation of vitamins, e.g. the abovementioned vitamins such as pantothenic acid and riboflavin, precursors and secondary products thereof.

Further preferred embodiments of the invention relate to the use of the aqueous glucose solution obtainable according to the invention in a production by fermentation of
  mono-, di- and tricarboxylic acids, in particular aliphatic mono- and dicarboxylic acids having 2 to 10 carbon atoms, such as acetic acid, propionic acid, fumaric acid and succinic acid;
  aliphatic hydroxycarboxylic acids having 3 to 10 carbon atoms such as lactic acid;
  long-chain alkanols as mentioned hereinbefore, in particular alkanols having 4 to 10 carbon atoms such as butanol;
  diols as mentioned hereinbefore, in particular alkanediols having 3 to 10 carbon atoms, and in particular 3 to 8 carbon atoms, such as propanediol;
  ketones as mentioned hereinbefore, in particular ketones having 3 to 10 carbon atoms such as acetone;
  amines, in particular aliphatic diamines having 3 to 10 carbon atoms, such as 1,5-diaminopentane;
  nucleotides such as 5'-IMP and 5'-GMP, and
  carbohydrates as mentioned hereinbefore, in particular disaccharides, such as trehalose, oligosaccharides and polysaccharides such as glucan.

In a further particularly preferred embodiment, the metabolic product produced by the microorganisms in the fermentation is polyhydroxyalkanoates such as poly(3-hydroxybutyrate) and copolyesters with other organic hydroxycarboxylic acids such as 3-hydroxyvaleric acid, 4-hydroxybutyric acid and others which are described in Steinbüchel (loc. cit.), e.g. also long-chain (also called longer-chain) hydroxycarboxylic acids such as 3-hydroxyoctanoic acid, 3-hydroxydecanoic acid and 3-hydroxytetradecanoic acid, and also mixtures thereof. For carrying out the fermentation, similar conditions and procedures can be employed here, as have been described for other carbon sources, e.g. in S. Y. Lee, Plastic Bacteria Progress and prospects for polyhydroxyalkanoate production in bacteria, Tibtech, vol. 14, (1996), pp. 431-438.

In a preferred embodiment, the microorganisms used in the fermentation are therefore selected from natural or recombinant microorganisms which overproduce at least one of the following metabolic products:
  enzymes such as phytase, xylanase or glucanase;
  amino acids such as lysine, threonine, glutamate or methionine;
  vitamins such as pantothenic acid and riboflavin; precursors and/or secondary products thereof;
  disaccharides such as trehalose;
  polysaccharides such as glucan;
  aliphatic mono- and dicarboxylic acids having 3 to 10 carbon atoms such as propionic acid, fumaric acid and succinic acid;
  aliphatic hydroxycarboxylic acids having 3 to 10 carbon atoms such as lactic acid;
  polyhydroxyalkanoates such as poly(3-hydroxybutyrate) and copolyesters of 3-hydroxybutyric acid;
  ketones having 3 to 10 carbon atoms such as acetone;
  amines, in particular aliphatic diamines having 3 to 10 carbon atoms such as 1,5-diaminopentane;
  alkanols having 4 to 10 carbon atoms such as butanol; and
  alkanediols having 3 to 8 carbon atoms such as propanediol.

Suitable microorganisms are customarily selected from the genera *Corynebacterium, Brevibacterium, Bacillus, Ashbya, Escherichia, Aspergillus, Alcaligenes, Actinobacillus, Anaerobiospirillum, Lactobacillus, Propionibacterium, Rhizopus, Clostridium, Schizophyllum* and *Sclerotium*, in particular from strains of *Corynebacterium glutamicum, Corynebacterium* sp AJ-1526, *Brevibacterium ammoniagenes, Bacillus subtilis, Bacillus megaterium, Ashbya gossypii, Escherichia coli, Aspergillus niger, Aspergillus terreus, Aspergillus itaconicus, Alcaligenes latus, Anaerobiospirillum succiniproducens, Actinobacillus succinogenes, Lactobacillus delbrückii, Lactobacillus leichmannii, Propionibacterium arabinosum, Propionibacterium schermanii, Propionibacterium freudenreichii, Clostridium propionicum, Clostridium formicoaceticum, Clostridium acetobutylicum, Rhizopus arrhizus, Rhizopus oryzae, Schizophyllum commune* and *Sclerotium rolfsii*.

In a preferred embodiment, the microorganism used in the fermentation is a strain of the genus *Corynebacterium*, in particular a strain of *Corynebacterium glutamicum*. In particular, it is a strain of the genus *Corynebacterium*, especially of *Corynebacterium glutamicum*, which overproduces an amino acid, especially lysine, methionine or glutamate.

In a further preferred embodiment, the microorganism used in the fermentation is a strain of the genus *Escherichia*, in particular a strain of *Escherichia coli*. In particular it is a strain of the genus *Escherichia*, especially of *Escherichia coli* which overproduces an amino acid, especially lysine, methionine or threonine.

In an especially preferred embodiment, the metabolic product produced by the microorganisms in the fermentation is lysine. For carrying out the fermentation, here similar conditions and procedures can be employed as have been described for other carbon sources, e.g. in Pfefferle et al., loc. cit., and U.S. Pat. No. 3,708,395. In principle, not only a continuous procedure but also a discontinuous (batch or fed-batch) procedure come into consideration, preference is given to the fed-batch procedure.

In a further particularly preferred embodiment, the metabolic product produced by the microorganisms in the fermentation is methionine. For carrying out the fermentation, here similar conditions and procedures can be employed as have been described for other carbon sources e.g. in WO 03/087386 and WO 03/100072. In the case of lysine production, a medium for the fermentation of lysine is produced therefor from the glucose solution obtained according to the invention together with nutrient salts and complex nutrient media components, e.g. molasses. This medium can be sterilized directly or indirectly via steam. After sterilization, the medium is used in a fermentation for producing lysine with customary microorganisms, e.g. *Corynebacterium glutamicum*. After completion of the fermentation, the fermentation broth, in addition to lysine, also comprises the microorganism (biomass), dissolved components of the nutrient medium and optionally also non-starch-comprising solid components of the starch source which could not be separated off completely by the solid/liquid separation (see chapter 2.2.3). Obtaining lysine can proceed in a conventional manner and is described in more detail further below.

In a further particularly preferred embodiment, the metabolic product produced by the microorganisms in the fermentation is pantothenic acid. For carrying out the fermentation, similar conditions and procedures can be employed here as have been described for other carbon sources, e.g. in WO 01/021772.

In a further particularly preferred embodiment, the metabolic product produced by the microorganisms in the fermentation is riboflavin. For carrying out the fermentation, similar conditions and procedures can be employed here as have been described for other carbon sources, e.g. in WO 01/011052, DE 19840709, WO 98/29539, EP 1186664 and Fujioka, K.: New biotechnology for riboflavin (vitamin B2) and character of this riboflavin. Fragrance Journal (2003), 31(3), 44-48.

In a further particularly preferred embodiment, the metabolic product produced by the microorganisms in the fermentation is fumaric acid. For carrying out the fermentation, similar conditions and procedures can be employed here as have been described for other carbon sources, e.g. in Rhodes et al., Production of Fumaric Acid in 20-L Fermentors, Applied Microbiology, 1962, 10 (1), 9-15.

In a further particularly preferred embodiment, the metabolic product produced by the microorganisms in the fermentation is lactic acid. For carrying out the fermentation, similar conditions and procedures can be employed here as have been described for other carbon sources, e.g. in Narayanan et al., Electronic J. Biotechnol. 2004, 7, http://www.ejbiotechnology.info/content/vol7/issue2/full/7/pdf.

In a further particularly preferred embodiment, the metabolic product produced by the microorganisms in the fermentation is succinic acid. For carrying out the fermentation, similar conditions and procedures can be employed here as have been described for other carbon sources, e.g. in Int. J. Syst. Bacteriol. 26, 498-504 (1976); EP 249773 (1987), inventors: Lemme and Datta; U.S. Pat. No. 5,504,004 (1996), inventors: Guettler, Jain and Soni; Arch. Microbiol. 167, 332-342 (1997); Guettler M V, Rumler D, Jain M K., *Actinobacillus succinogenes* sp. nov., a novel succinic-acid-producing strain from the bovine rumen. Int J Syst Bacteriol. 1999 January; 49 Pt 1:207-16; U.S. Pat. No. 5,723,322, U.S. Pat. No. 5,573,931, U.S. Pat. No. 5,521,075, WO 99/06532, U.S. Pat. No. 5,869,301 or U.S. Pat. No. 5,770,435.

In a further particularly preferred embodiment, the metabolic product produced by the microorganisms in the fermentation is itaconic acid. For carrying out the fermentation, similar conditions and procedures can be employed here as have been described for other carbon sources, e.g. in Kautola, H., Appl. Microb. Biotechnol., 1990, 33, 7 and Willke et al., Appl. Microbiol. Biotechnol., 2001, 56, 289.

In a further particularly preferred embodiment, the metabolic product produced by the microorganisms in the fermentation is a phytase. For carrying out the fermentation, similar conditions and procedures can be employed here as have been described for other carbon sources, e.g. in WO 98/55599.

In a further particularly preferred embodiment, the metabolic product produced by the microorganisms in the fermentation is glucan. For carrying out the fermentation, similar conditions and procedures can be employed here as have been described for other carbon sources, e.g. in Schilling et al.: Repression of oxalic acid biosynthesis in the unsterile scleroglucan production process with *Sclerotium rolfsii* ATCC 15205, Bioprocess Engineering 22 (2000), 51-55 or Rau et al.: Oxygen controlled batch cultivations of *Schizophyllum commune* for enhanced production of branched β-1,3-glucans, Bioprocess Engineering 11 (1994), 161-165.

In a further particularly preferred embodiment, the metabolic products produced by the microorganisms in the fermentation are nucleotides such as 5'-IMP and 5'-GMP. For carrying out the fermentations, similar conditions and procedures can be employed here as have been described for other carbon sources, e.g. in Sato et al., Accumulation of Guanosine Polyphosphates by *Brevibacterium* ammoniagenes: Isolation and Identification of the Products. Agr. Biol. Chem. 40 (3), 1976, 465-474; Mori et al: A novel process of inosine 5'-monophosphate production using overexpressed guanosine/inosine kinase. Appl. Microbiol. Biotechnol. (1997) 48: 693-698, or GB 01188885.

In a further particularly preferred embodiment, the metabolic product produced by the microorganisms in the fermentation is glutamate. For carrying out the fermentations, similar conditions and procedures can be employed here as have been described for other carbon sources, e.g. in E. Kimura, L-Glutamate Production, in: Handbook of *Corynebacterium glutamicum*, CRC press, Boca Raton, Fla., 439-464.

In a further particularly preferred embodiment, the metabolic product produced by the microorganisms in the fermentation is 1,5-diaminopentane. For carrying out the fermentations, similar conditions and procedures can be employed here as have been described for other carbon sources, e.g. in JP 2004222569.

In a further particularly preferred embodiment, the metabolic product produced by the microorganisms in the fermentation is 5-ketogluconic acid. For carrying out the fermentation, similar conditions and procedures can be employed here as have been described for other carbon sources, e.g. in Elfari, M. et al., Appl. Microbiol. Biotechnol. 2005, 66, 668, and Herrmann U., et al., Appl. Microbiol. Biotechnol. 2004, 64, 86.

In a further particularly preferred embodiment, the metabolic product produced by the microorganisms in the fermentation is 5-ketogluconic acid. For carrying out the fermentation, similar conditions and procedures can be employed here as have been described for other carbon sources, e.g. in Elfari, M. et al., Appl. Microbiol. Biotechnol. 2005, 66, 668, and Herrmann U., et al., Appl. Microbiol. Biotechnol. 2004, 64, 86.

In a further particularly preferred embodiment, the metabolic product produced by the microorganisms in the fermentation is 2,5-diketogluconic acid. For carrying out the reaction, similar conditions and procedures can be employed here as have been described for other carbon sources, e.g. in Roper, H., Starch-Starke 1990, 42, 342 or Zelic, B. et al., Chem. Biochem. Eng. Q. 2002, 16, 7.

Workup of the Fermentation

The method according to the invention for producing an organic substance by fermentation yields a fermentation broth which, in addition to the desired metabolic product, comprises essentially the biomass generated during the fermentation and unutilized sugars, and also unutilized buffer salts and nutrient salts. Generally, therefore, further processing of the fermentation broth follows the fermentation in order to obtain the valuable product, i.e. the organic substance produced by the fermentation method and converted into a handlable or tradable form and also to dispose of or feed to further utilization the by-products such as biomass and the aqueous components occurring in the fermentation.

The type of workup and the steps necessary therefor depend in a manner known per se on the material properties of the fermentation broth, and in particular on the type of metabolic products produced.

Typically, workup methods have one or more of the following steps which can be connected together in any desired sequence and expression:
 deactivating the microorganism, e.g. by sterilization in the manner described hereinbefore;
 separating off the biomass from the fermentation broth;
 isolating the nonvolatile metabolic product from the fermentation broth which still comprises biomass or is already separated off from the biomass;
 purifying the desired metabolic product;
 concentrating the metabolic product;
 concentrating the biomass.

The steps in this case need not all be a compulsory component of the workup method. For example, additional purification of the metabolic product or products can be dispensed with if high demands are not made of the purity of the product.

The biomass is separated off from the fermentation broth by customary methods of solid-liquid phase separation (e.g. described in Belter, P. A, Bioseparations: Downstream Processing for Biotechnology, John Wiley & Sons (1988), and Ullmann's Encyclopedia of Industrial Chemistry, $5^{th}$ edition on CD-ROM, Wiley-VCH) and generally proceeds by mechanical methods such as decanting, separation, flotation, centrifugation, sedimentation, filtration or membrane methods. In this case, multistage connection of a method or combinations of different methods are also conceivable, such as, e.g. decanting and separation. In addition, wash water can also be used in order to increase the yield of the nonvolatile metabolic product in separating off biomass. Preferably, the abovementioned methods are used when the metabolic product is a substance which is present in solution in the fermentation broth. In the case of oily or solid metabolic products, mechanical separation by means of decanting, separation, flotation, centrifugation, sedimentation, is generally expedient when there are density differences between the biomass and the metabolic product. Otherwise, in particular chromatographic methods, distillation methods or extraction methods then come into consideration too.

The valuable product is isolated or depleted from the fermentation broth generally in such a manner that at least one valuable product is depleted or isolated from the fermentation broth in such a manner that the content of this valuable product in the remaining fermentation broth is a maximum of 20% by weight, in particular a maximum of 10% by weight, especially a maximum of 5% by weight, and very especially a maximum of 2.5% by weight, in each case based on the total weight of the remaining feimentation broth. The valuable product can be isolated or depleted from the fermentation broth in one or more steps.

For isolating a valuable product dissolved in the fermentation broth, advantageously a procedure is followed such that first the biomass and other undissolved components are removed from the fermentation broth, e.g. by means of centrifugation or filtration, and then the valuable product is isolated from the liquid phase, e.g. by crystallization, precipitation, adsorption, distillation, chromatography, extraction, ion exchange, membrane methods (preferably diffusion dialysis, electrodialysis, nanofiltration). Alternatively, the valuable product can also be isolated directly from the fermentation broth, e.g. by using chromatographic methods, extraction methods, membrane methods, adsorption methods and distillation. A chromatographic method which may be mentioned, in particular, is ion-exchange chromatography in which the valuable product can be selectively isolated from the chromatographic column.

For separating off the valuable product it can be expedient to modify the valuable product chemically in the fermentation broth in a first step, e.g. by esterification or salt formation, in order thereby to improve the separability.

Crystallization is a method which enables not only separation of the valuable product from the fermentation broth, but also further purification of the valuable product. It is then employed preferably in combination with a mechanical separation, as already mentioned hereinbefore, in which the crystals are separated off from the mother liquor.

In the case of volatile or oily compounds, generally control of the maximum temperatures during workup, in particular during drying, is necessary. Advantageously, these compounds can also be isolated by formulating them in semi-solid form (pseudosolid form) on adsorbents. Adsorbents suitable for this purpose are specified, e.g. in WO 2005/116228 of the applicant, for example activated carbons, aluminum oxides, silica gels, silica, clay, soots, zeolites, inorganic alkali metal salts and alkaline earth metal salts such as sodium, potassium, magnesium and calcium hydroxides, carbonates, silicates, sulfates, phosphates, in particular magnesium salts and calcium salts, e.g. $Mg(OH)_2$, $MgCO_3$, $MgSiO_4$, $CaSO_4$, $CaCO_3$, alkaline earth metal oxides, e.g. MgO and CaO, other inorganic phosphates and sulfates, e.g. $ZnSO_4$, salts of organic acids, in particular alkali metal salts and alkaline earth metal salts thereof, and especially sodium and potassium salts thereof, e.g. sodium and potassium acetate, formate, hydrogenformates and citrate, higher-molecular-weight organic supports such as optionally modified starches, cellulose, lignin which are further below in combination with the support materials mentioned with the product formulation and also the gluten according to the invention. Examples of valuable products which can be advantageously isolated in this manner are γ-linolenic acid, dihomo-γ-linolenic acid, arachidonic acid, eicosapentaenoic acid and docosahexaenoic acid, in addition propionic acid, lactic acid, propanediol, butanol and acetone. These compounds in pseudosolid formulation are also taken to mean nonvolatile metabolic products or valuable products in solid form in the context of the present invention.

The abovementioned process steps of workup can sometimes require the use of additives (e.g. for regeneration of the ion exchanger, the solvent for the extraction etc.) and/or a by-product stream can sometimes occur (e.g. mother liquor of the crystallization, eluate of the ion exchanger). These by-product streams which can in some cases still comprise the valuable product, the biomass, non-starch-comprising solid components of the wheat used as starch source and proportions of the additives, can either be worked up further, in part recycled to some process step in the overall process, disposed of or further used.

All of the abovementioned streams, preferably the biomass-comprising streams, the valuable-product-comprising streams and also the product streams comprise in some circumstances high water concentrations (owing to fermentation or wash water in the workup) and can be concentrated (reduction of water content). This can be achieved thermally, e.g. by means of concentration by evaporation, drying, or mechanically by means of membrane processes, filtration etc.

The water can be disposed of or recirculated as process water, and used, e.g. for slurrying the endosperm fraction or for slurrying the solid which is separated off in the multistage gluten separation.

A further special embodiment relates to a method in which the volatile components of the fermentation broth are substantially or completely removed without previous isolation or depletion of the valuable product, and optionally without previous separation of the biomass, wherein a solid formulation of the valuable product is obtained. A more precise description for carrying out such a method may be found in the applicant's WO 2007/028804, which is hereby incorporated herein by reference.

By adding formulation aids such as support and coating materials, binders and also other additives, the properties of the dried valuable product which is present together with the solid components of the fermentation can be customized in a manner known per se specifically with respect to various parameters such as active ingredient content, particle size, particle shape, tendency to dust formation, hygroscopicity, stability, in particular storage stability, color, odor, flow behavior, agglomeration tendency, electrostatic charge, sensitivity to light and temperature, mechanical stability and redispersibility.

The customarily used formulation aids include, e.g. binders, support materials, powdering aids/flow aids, in addition color pigments, biocides, dispersants, antifoams, viscosity regulators, acids, lyes, antioxidants, enzyme stabilizers, enzyme inhibitors, adsorbates, fats, fatty acids, oils or mixtures thereof. Such formulation aids are used advantageously as drying aids, in particular when formulation and drying methods such as spray drying, fluidized-bed drying and freeze drying are used. For further details, reference may be made to WO 2007/028804.

The proportion of the abovementioned additives, and optionally other additives such as coating materials, depending on the special requirements of the respective valuable product, and also depending on the properties of the additives used, can vary greatly and can be, e.g., in the range from 0.1 to 80% by weight and in particular in the range from 1 to 30% by weight, in each case based on the total weight of the finished formulated product or mixture of matter.

Formulation aids can be added before, during or after the workup of the fermentation broth (also called product formulation or solid design) and in particular during drying. Addition of formulation aids before workup of the fermentation broth or of the valuable product can be advantageous, in particular, in order to improve the processability of the substances or products to be worked up. The formulation aids can be added not only to the valuable product obtained in solid form but also to a solution or suspension comprising this valuable product, e.g. after completion of fermentation, directly to the fermentation broth or to a solution or suspension obtained in the course of workup before the concluding drying step.

Thus the auxiliaries can be added, e.g. to a suspension of the valuable product; such a suspension can also be added to a support material, e.g. by spraying or mixing. The addition of formulation aids during drying can play a role, e.g. when a solution or suspension comprising the valuable product is sprayed. Formulation aids are added, in particular after drying, e.g. in the application of coverings or coatings/coating layers to dried particles. Not only after drying but also after any possible coating step, further auxiliaries can be added to the product.

The volatile components are removed from the fermentation broth in a manner known per se by customary methods for separating off solid phases from liquid phases, including filtration methods and methods for evaporating volatile components of the liquid phases. Such methods which can also comprise steps for coarse purification of the valuable substances and also steps for customizing, are described, e.g., in Belter, P. A, Bioseparations: Downstream Processing for Biotechnology, John Wiley & Sons (1988), and Ullmann's Encyclopedia of Industrial Chemistry, $5^{th}$ edition on CD-ROM, Wiley-VCH. Methods, apparatuses, auxiliaries and general and special embodiments known to the skilled worker and usable in the context of product formulation or workup after completion of fermentation are further described in EP 1038 527, EP 0648 076, EP 835613, EP 0219 276, EP 0394 022, EP 0547 422, EP 1088 486, WO 98/55599, EP 0758 018 and WO 92/12645.

In a first variant of this embodiment, the generally nonvolatile valuable product, if it is present in dissolved form in the liquid phase, is converted from the liquid phase to the solid phase, e.g. by crystallization or precipitation. Subsequently, the nonvolatile solid components including the valuable product are separated off, e.g. by means of centrifugation, decanting or filtration. In a similar manner, oily valuable products can also be separated off, wherein the respective oily fermentation products can be converted to a solid form by adding adsorbents, e.g. silica, silica gels, mud, clay and activated carbon.

In a second variant of this embodiment, the volatile components are removed by evaporation. The evaporation can proceed in a manner known per se. Examples of suitable methods for evaporating volatile components are spray drying, fluidized-bed drying and fluidized-bed agglomeration, freeze drying, flash dryers and contact dryers, and also extrusion drying. A combination of the abovementioned methods with shaping methods such as extrusion, pelleting or prilling can also be performed. In the case of these last-mentioned methods, preferably partly or substantially predried valuable-product-comprising mixtures of matter are used.

In a preferred embodiment, the removal of the volatile components of the fermentation broth comprises a method for spray drying or a method of fluidized-bed drying, including fluidized-bed granulation. For this the fermentation broth, optionally after a preseparation for removal of coarse solid particles which do not comprise valuable product or comprise only small proportions of nonvolatile valuable product, are fed to one or more spray- or fluidized-bed-drying apparatuses. The transport or feed of the solids-loaded fermentation broth is expediently performed by means of customary transport devices for solids-containing liquids, e.g. pumps such as eccentric screw pumps (e.g. from Delasco PCM) or high-pressure pumps (e.g. from LEWA Herbert Ott GmbH).

In the special case of producing lysine, the workup method generally comprises separating off the biomass by separators. The biomass-comprising fraction is then dried, e.g. in drum dryers or tube-bundle dryers. Optionally, before the drying, a fermentation residue of the vitamin $B_2$ fermentation, called "BFR" (vitamin $B_2$ fermentation residues) is added to the biomass-comprising fraction. The low-solids fraction is then generally acidified and passed through an ion exchanger. The lysine is bound on this ion exchanger. The lysine-depleted fermentation broth which leaves the ion exchanger is usually concentrated by evaporating water, solids which crystallized out in the course of this are separated off and dried. The resultant product is termed "fertilizer" and can be recirculated to the process or used as fertilizer and for other applications. The mother liquor of the crystallization is fed as condensed molasses solubles (CMS) to further processing. The lysine which is bound to the ion exchanger is eluted with ammonia water and concentrated by evaporating off water. Lysine can be taken off from this concentrated broth as a free base in the form of a liquid formulation. In the next process step the lysine is crystallized out as lysine hydrochloride by adding hydrochloric acid. The crystals are separated off by centrifugation and dried. The mother liquor of the crystallization is either recirculated to the eluate of the ion exchanger or can be taken off as lysine in a liquid formulation.

As an alternative to the described workup, the lysine-comprising fermentation broth is directly spray dried after the fermentation. Optionally, the fermentation residue can be added to the vitamin $B_2$ production. A possible single-stage or multistage preevaporation of the fermentation broth can lead to reduction of energy costs and capital costs.

Use of the Glucose in a Reaction Not Involving Fermentation

The invention further preferably relates to the use of the glucose solution obtainable according to the invention as a glucose source for the production of an organic substance, as defined above, not involving fermentation.

Accordingly, the invention further relates to a method for producing an organic substance by reaction not involving fermentation, comprising the following steps:
  i. providing an aqueous glucose solution according to the invention, e.g. by producing the glucose solution according to the method according to the invention and
  ii. using the glucose solution or an essentially water-free glucose obtained by concentrating the glucose solution according to the invention (water content <10% by weight) in a reaction not involving fermentation for producing the desired organic substance.

The reaction not involving fermentation can be carried out in a customary manner known to those skilled in the art. For this the aqueous glucose solution produced according to the invention or an essentially water-free glucose obtained by concentrating the glucose solution according to the invention is generally optionally reacted using a catalyst.

In a particularly preferred embodiment, the organic substance which is producible from glucose by a method not involving fermentation is 5-hydroxymethlyfurfural. For carrying out the reaction, similar conditions and procedures can be employed here as have been described for other carbon sources, e.g. in Cottier et al., Trends Heterocycl. Chem. 1991, 2, 233; Lewkowski, J., Arkivoc 2001, 2, 17; Kuster, B. F. M. et al., Carbohydr. Res. 1977, 54, 159, EP 0230250, FR 2464260 or DE 3601281.

In a further particularly preferred embodiment, the organic substance which is producible from glucose in a manner not involving fermentation is laevulinic acid. For carrying out the reaction, similar conditions and procedures can be employed here as have been described for other carbon sources, e.g. in Horvat et al, Tetrahedron Lett. 1985, 26, 2111 or U.S. Pat. No. 3,258,481.

In a further particularly preferred embodiment, the organic substance which is producible from glucose in a manner not involving fermentation is gluconic acid. For carrying out the reaction, similar conditions and procedures can be employed here as have been described for other carbon sources, e.g. in Lichtenthaler, F. W., Acc. Chem. Res. 2002, 35, 728, Besson, M. et al., J. Catal. 1995, 152, 116 or EP 233816.

In a further particularly preferred embodiment, the organic substance which is producible from glucose in a manner not involving fermentation is glucuronic acid. For carrying out the reaction, similar conditions and procedures can be employed here as have been described for other carbon sources, e.g. in Corma, A. et al., Chemical Routes for the Transformation of Biomass into Chemicals., Chem. Rev. 2007, 107, 2411-2502.

In a further particularly preferred embodiment, the organic substance which is producible from glucose in a manner not involving fermentation is 2-ketogluconic acid. For carrying out the reaction, similar conditions and procedures can be employed here as have been described for other carbon sources, e.g. in US 2002177198, WO 9915673 or EP 867446.

In a further particularly preferred embodiment, the organic substance which is producible from glucose in a manner not involving fermentation is glutaric acid. For carrying out the reaction, similar conditions and procedures can be employed here as have been described for other carbon sources, e.g. in Besson, M. et al., Reel. Tray. Chim. Pys-Bas 1996, 115, 217 and Dirkx, J. M. H. et al., J. Catal. 1981, 67, 1.

In a further particularly preferred embodiment, the organic substance which is producible from glucose in a manner not involving fermentation is sorbitol. For carrying out the reaction, similar conditions and procedures can be employed here as have been described for other carbon sources, e.g. in Dechamp, N. et al., Catal. Today 1995, 24, 29 and Maranhao, L. C. A. et al., Ind. Eng. Chem. Res. 2005, 44, 9624, WO 02100537, WO 02100539 and WO 2004052813.

In a further particularly preferred embodiment, the organic substance which is producible from glucose in a manner not involving fermentation is isosorbide. For carrying out the reaction, similar conditions and procedures can be employed here as have been described for other carbon sources, e.g. in WO 9804540, WO 9200947 and U.S. Pat. No. 4,297,290.

In a further particularly preferred embodiment, the organic substance which is producible from glucose in a manner not involving fermentation is alkylpolyglucosides. For carrying out the reaction, similar conditions and procedures can be employed here as have been described for other carbon sources, e.g. in U.S. Pat. No. 5,480,979 and U.S. Pat. No. 5,698,684.

In a further particularly preferred embodiment, the organic substance which is producible from glucose in a manner not involving fermentation is high-fructose corn syrup (HFCS). For carrying out the reaction, similar conditions and procedures can be employed here as have been described for other carbon sources, e.g. in Marshall et al., Enzymatic Conversion of d-Glucose to d-Fructose 1957, Science 125 (3249), 648 and U.S. Pat. No. 4,523,960.

Formulating the By-Products

As already explained above, a number of material streams occur as by-products or coupled products not only in steps a) and c) of the method according to the invention of glucose production, but also in the further processing of the glucose by fermentation to give valuable products. Generally, these are one or more of the following material streams, preferably in the amounts stated:
  dusty fines proportion of the grain cleaning, where occurring, typically in an amount up to 5% by weight, in particular 0.1 to 3% by weight;
  bran, typically in an amount up to 7% by weight, e.g. 1 to 6% by weight;
  gluten, typically in an amount from 1 to 20% by weight, comprising vital gluten, typically in an amount from 0 to 10% by weight, preferably 2 to 6% by weight, and/or gluten from the glucose, typically in an amount from 1 to 15% by weight, preferably 2 to 10% by weight,
  biomass, typically in an amount from 1 to 40% by weight, preferably 5 to 20% by weight and
  optionally by-product streams which can occur in the processes for working up the valuable product, where occurring, typically in an amount up to 100% by weight, preferably 0.2 to 50% by weight, particularly preferably 0.3 to 20% by weight, wherein all % by weight figures relate to the total mass of the grain used for glucose production.

These material streams can be processed separately or fed to disposal. It is likewise possible to mix these material streams with one another in any desired combination, i.e. in part or completely (i.e. bringing together at least two material streams) in the context of further processing. Generally, before the further processing drying proceeds, wherein optionally the material streams which are to be mixed with one another are dried before mixing or after mixing. Frequently, a procedure is followed such that the solid particles of the material streams which are at least in part freed from water are agglomerated or milled together.

The process steps drying, agglomerating and milling can be carried out and combined optionally in any desired sequence for mixing various streams. Preferably, a procedure is followed such that, during mixing of the material streams a by-product is obtained which is preferably suitable for feed and comprises at least a proportion of the material streams of wheat processing (e.g. sugar production) and comprises at least one component from the workup of the fermentation broth (biomass or by-product streams).

Optionally, formulation aids, active ingredients or one or more biomasses or one or more by-product streams of other fermentation processes can be added to the by-products thus produced, wherein this addition can take place at any desired point of the method.

The residual moisture contents of these by-products are, in the undried state, 10 to 90% by weight, preferably 40 to 80% by weight. In the dried state the residual moisture contents of the by-products are 1 to 20% by weight, preferably 3 to 18% by weight, and particularly preferably 5 to 15% by weight.

The median particle diameters of the solid proportion of the by-products is between 50 µm and 8 mm, preferably between 100 µm and 5 mm, and particularly preferably between 150 µm and 3 mm.

If a by-product is a mixture of various solid fractions, before mixing, the particle size distributions of the individual material streams of which the by-product is composed are generally selected or set in such a manner that separation of the material streams does not occur or at least remains low. This is generally ensured when the material streams to be mixed have a particle size as similar as possible, or when what is termed the SPAN value of the by-product mixture is less than 4, preferably less than 3, particularly preferably less than 2, and in particular less than 1.8. In this case, the SPAN value of the by-product mixture is defined as $$\text{SPAN} = (D_{90} - D_{10})/D_{50}$$

The $D_{50}$ value in this case is the weighed mean particle diameter of the by-product mixture, i.e. based on the mass, the $D_{50}$ value gives the particle diameter which 50% by weight of the particles are greater than and 50% by weight are smaller than. The $D_{90}$ value is the diameter which 90% by weight of the particles are smaller than and 10% by weight of the particles are greater than. The $D_{10}$ value is the diameter which 10% by weight of the particles are smaller than and 90% by weight of the particles are greater than. The Span value and the particle diameters and their distribution can be determined in a manner known per se, e.g. by sieve analysis or by light scattering.

If a by-product is produced from at least one dry material stream and at least one liquid stream, firstly the liquid material streams can be dried first and thereafter treated as solid streams (see above). For the mixture of these material streams the same applies as for mixing the already originally dry material streams. Secondly, however, the liquid and dry material streams can be mixed with one another before drying or during drying. This has the advantage that the solid present in the liquid or suspension-like material stream is readily mixed and distributed into the dry material streams, or the liquid material stream is applied as coating to the solid components of the dry material streams or the liquid material streams are used in order to agglomerate or bind the solid particles of the dry material stream.

In one embodiment of the invention, the dusty fines proportion is discarded and not mixed into the by-products.

In one embodiment of the invention, the bran is not mixed into the by-products, but is used as an independent product.

In one embodiment of the invention, the gluten is not mixed into the by-products but is used as an independent product.

In one embodiment of the invention, the biomass is not mixed into the by-products, but is used as an independent product.

In one embodiment of the invention, the by-product streams are not mixed into the by-products, but are used or discarded or disposed of as independent products.

In a particular embodiment of the invention, a proportion or the entire amount of the resultant bran, for example 10 and 100% by weight, based on dry matter content of all of the bran which occurs, is mixed with at least one by-product stream, e.g. with 10 to 100% by weight, based on the respective by-product stream and dried, in order in this manner to obtain a bran-comprising by-product. Optionally, the bran can be milled before the mixing, such that median particle sizes of 150 to 1400 µm, particularly preferably 200 µm to 800 µm, are set. A further option is to add to the bran some of the resultant dusty fines proportion of the wheat, e.g. 10 to 100% by weight, before or after the milling.

In a method for the production of lysine by fermentation, for example syrup-like by-product stream CMS occurs, having a dry matter proportion from 40 to 90% by weight, which can be mixed or combined with the bran, e.g. by means of spraying and then can be dried together. After drying, optionally comminution of resulting agglomerates can be performed. The composition (based on the dry matter) of the by-product obtained in this manner is generally as follows:

Crude protein: 5 to 60% by weight, preferably 10 to 50% by weight,

Starch: 1 to 50% by weight, preferably 5 to 40% by weight,

Crude fiber: 1 to 20% by weight, preferably 2 to 10% by weight,

Crude fat: 1 to 20% by weight, preferably 1 to 10% by weight,

Crude ash: 0 to 15% by weight, preferably 0.1 to 7% by weight and

Lysine: 0 to 10% by weight, preferably 0 to 5% by weight.

In a further particularly preferred embodiment of the invention, a by-product A is produced in which in each case 10 to 100% by weight, preferably 30 to 100% by weight, particularly preferably the total amount of the resultant gluten, and also 10 to 100% by weight, preferably 30 to 100% by weight, particularly preferably the total amount of the resultant biomass are mixed with one another. Optionally this by-product can comprise a proportion of 0 to 100% by weight of the resultant bran and 0 to 100% by weight of the fines proportion.

For producing this by-product A, the following method variants are possible.

In a first variant, all streams (gluten, biomass and optionally bran and/or fines proportion) are mixed and dried.

Optionally, the dry by-product or the dry feed material bran can also further be milled, in such a manner that a median particle size and a residual moisture content, as described above, can be set. In a second variant, only the moist streams of the gluten and the biomass are first mixed, and then dried together. This has the advantage that the dry bran need not be passed unnecessarily through the dryer. After drying the components, either all streams can be mixed directly, or first the individual streams can be milled and then mixed. After mixing, again milling can follow. A median particle size and a residual moisture content as described above can be set. In a third variant, the two moist streams of the biomass and gluten are first dried separately. This can have the advantage that unwanted decomposition reactions such as, e.g., a Maillard reaction between sugar and protein components, which can be present in the streams, are avoided or reduced. The dry streams of the gluten, biomass and optionally bran can optionally be milled and mixed, or optionally milling can follow the mixing. A median particle size and a residual moisture content as described above can be set. In a fourth variant, a proportion of 10 to 100% of at least one resultant solid stream is fed during or before the drying to at least one stream which is to be dried. This has the advantage that desired agglomerates can be formed, the flow behavior of the product is improved, or the dusting tendency of the product is decreased. For instance, the gluten occurring in the moist state (or proportions thereof) can be mixed before or during the drying with proportions of bran (optionally milled) or proportions of fines portion or any desired combinations thereof. There is likewise the possibility of mixing, before or during the drying, the biomass occurring in the moist state (or proportions thereof) with proportions of bran (optionally milled) or proportions of fines portion or any desired combinations thereof.

In a special embodiment of the invention, in the production of the by-product A biomass from the lysine fermentation is used. The streams gluten and biomass are used in an amount of in each case 50 to 100% by weight, based on the total amount of the stream occurring respectively, and processed to form a by-product using the above-described methods. This by-product is novel and is likewise subject matter of the invention. The preferred composition (based on the dry matter) of the by-product is characterized as follows:

Crude protein: 10 to 60% by weight, particularly preferably 20 to 50% by weight,
Total sugars: 0.1 to 50% by weight, particularly preferably 5 to 45% by weight,
Crude fiber: 0 to 10% by weight, particularly preferably 0 to 7% by weight,
Crude fat: 1 to 30% by weight, particularly preferably 5 to 20% by weight,
Crude ash: 0 to 15% by weight, particularly preferably 0.1 to 7% by weight and
Lysine: 0.1 to 20% by weight, particularly preferably 0.2 to 10% by weight.

In a further embodiment of the production of the by-product A, the biomasses of differing fermentations are mixed. In this manner the various biomasses can also again be first dried separately from one another or mixed and then dried together. The biomasses can be mixed with one another in any desired mixing ratio. Preferably, 30 to 100%, preferably 50 to 100%, of the resultant biomass of a respective fermentation is mixed with one another here.

In a further embodiment of the invention, at least one biomass of a further fermentation process is added to any desired (above-described) by-product at any desired point of the production process. In a particular embodiment, a by-product which comprises not only biomass of a lysine fermentation (and also above-described) and biomass of a $B_2$ fermentation (BFR, and also abovedefined) is involved. Preferably, 30 to 100%, preferably 50 to 100%, of the resultant biomass of a respective fermentation is mixed together here. Optionally, the by-product comprises proportions of 50 to 100% of the resultant wheat germ and/or 50 to 100% of the resultant gluten and/or 50 to 100% of the resultant bran and also 0 to 100% of the resultant fines proportion.

In a further embodiment, this is a by-product which comprises not only biomass from a chemical fermentation, such as, e.g., a lysine fermentation, or a glutamate fermentation, but also biomass from a bioethanol fermentation.

Mixing the at least 2 biomasses involves, in a particular embodiment of the invention, biomasses from fermentations, each of which is operated with a glucose stream obtained from the wheat starch saccharification according to the invention. In this case a procedure can be followed such that the two fermentations involve the same glucose stream. In another embodiment, in each case the glucose streams obtained from methods according to the invention are used, but these are separately produced glucose streams generally having different purities of glucose. The at least 2 glucose streams differ in this case typically in the concentration of the non-starch-comprising solid components. Based on the dry matter, at least one stream is formed having a high proportion, and one stream having a low proportion, of non-starch-comprising solid components. The different purities of the glucose streams can be generated by means of methods such as decanting, separation, centrifugation, sedimentation, filtration or membrane processes. Multistage connections of a method or combinations of different methods are also conceivable, such as, e.g., decanting and separation.

However, the fermentations can also be based on different carbohydrate sources (carbon sources), wherein at least one carbon source is a glucose which is obtainable by the method according to the invention.

A by-product which comprises at least the biomass of two different fermentations can also comprise at least 2 different metabolic products.

Similarly to the above-described by-product A comprising gluten, corn germ and biomass (optionally bran) and the associated production method, by-products can also be produced which comprise, as dry components, only gluten and biomass (optionally bran and/or formulation aids). Possible production methods are similar to the abovementioned.

All by-products can in addition comprise formulation aids, dietary fiber, fillers or other active ingredients which are added to any desired process step of the production.

By adding formulation aids such as support and coating materials, binders and also other additives, the properties of the by-product can be specifically customized in a manner known per se with respect to various parameters such as grain size, particle shape, dusting tendency, hygroscopicity, stability, in particular storage stability, color, odor, flow behavior, agglomeration tendency, electrostatic charge, light and temperature sensitivity, mechanical stability and redispersibility.

The formulation aids customarily used include, e.g., binders, support materials, powdering/flow aids, in addition color pigments, biocides, dispersants, antifoams, viscosity-regulating agents, acids, lyes, antioxidants, enzyme stabilizers, enzyme inhibitors, adsorbates, fats, fatty acids, oils or mixtures thereof. Such formulation aids are used as drying aids advantageously, in particular when formulation and drying methods such as spray drying, fluidized-bed drying and freeze drying are used.

Examples of binders are carbohydrates, in particular sugars such as mono-, di-, oligo- and polysaccharides, e.g. dextrins, trehalose, glucose, glucose syrup, maltose, sucrose, fructose and lactose; colloidal substances such as animal proteins, e.g. gelatin, casein, in particular sodium caseinate, vegetable proteins, e.g. soy protein, pea protein, bean protein, lupin, zein, wheat protein, corn protein and rice protein, synthetic polymers, e.g. poly(ethylene glycol), poly(vinyl alcohol) and in particular the collidone brands of BASF, optionally modified biopolymers, e.g. lignin, chitin, chitosan, polylactide and modified starches, e.g. octenylsuccinate anhydride (OSA); gums, e.g. acacia gum; cellulose derivatives, e.g. methylcellulose, ethylcellulose, (hydroxyethyl)methylcellulose (NEMC), (hydroxypropyl)methylcellulose (HPMC), carboxymethylcellulose (CMC); flours, e.g. flour, wheat flour, rye flour, barley flour and rice flour.

Examples of support materials and also fibers or fillers are carbohydrates, in particular the sugars mentioned above as binders and also starches, e.g. of corn, rice, potatoes, wheat and cassava; modified starches, e.g. octenylsuccinate anhydride; cellulose and microcrystalline cellulose; inorganic minerals or loam, e.g. clay, coal, kieselguhr, silica, tallow and kaolin; semolina, e.g. wheat semolina, bran, e.g. wheat bran, the flours mentioned above as binders; salts such as metal salts, in particular alkali metal and alkaline earth metal salts of organic acids, e.g. Mg, Ca, Zn, Na, K citrate, acetate, formate and hydrogenformates, inorganic salts, e.g. Mg, Ca, Zn, Na, K sulfates, carbonates, silicates or phosphates; alkaline earth metal oxides such as CaO and MgO; inorganic buffering agents such as alkali metal hydrogenphosphates, in particular sodium and potassium hydrogenphosphates, e.g. $K_2HPO_4$, $KH_2PO_4$ and $Na_2HPO_4$; and also generally the adsorbents mentioned in connection with the production according to the invention of metabolic products having a low melting point or oily consistency. Further fillers or fibers can also be fatty products, such as, e.g., soy flour, soy meal or flours or meals of corn, rye, wheat, barley or peas.

Examples of powdering agents or flow aids are kieselguhr, silica, e.g. the Sipernat brands from Degussa; clay, clay minerals, sepiolites, kenites, montmorillonites, zeolites, coal, tallow and kaolin; the starches mentioned above as support materials, modified starches, inorganic salts, salts of organic acids and buffering agents; cellulose and microcrystalline cellulose.

Examples which may be mentioned with respect to other additives are: color pigments such as $TiO_2$; biocides; dispersants; antifoams; viscosity-regulating agents; inorganic acids such as phosphoric acids, nitric acid, hydrochloric acid, sulfuric acid; organic acids such as saturated and unsaturated mono- and dicarboxylic acids, e.g. formic acid, acetic acid, propionic acid, butyric acid, valeric acid, palmitic acid, stearic acid, oxalic acid, malonic acid, succinic acid, glutaric acid, adipic acid, pimelic acid, maleic acid and fumaric acid; lyes such as alkali metal hydroxides, e.g. NaOH and KOH; antioxidants; enzyme stabilizers; enzyme inhibitors; adsorbates; fats; fatty acids and oils.

The proportion of the abovementioned additives and optionally other additives such as coating materials can vary greatly according to the special requirements of the respective by-product and also in dependence on the properties of the additives used, and can be, e.g., in the range from 0.1 to 80% by weight, based on the total weight of the formulated product.

The addition of formulation aids can proceed at any desired production step of the by-product, in particular during the optionally required drying. The formulation aids can be added not only to the by-product obtained in solid form but also to a solution or suspension containing it. In particular, after drying, formulation aids are added, e.g. on application of coverings or coatings/coating layers to dried particles. Both after drying and also after any coating step, further auxiliaries can be added to the product.

Optionally, in addition to the respective metabolic product of the fermentation, other active ingredients can be added to the by-products, preferably active ingredients customary in the feed industry, at any desired step of the production method. Active ingredients here are taken to mean all vitamins, (preferably A, B1, B2, B5, B6, C, D3 and E), carotenoids, enzymes (preferably phytase, xylanase, glucanase, amylase, cellulase, hemicellulase, protease, lipase, pectinase, phosphatases), probiotics (e.g. *Enterococus* ssp., *Lactobacillus* ssp. *Bacillus* ssp., *Pediococus* ssp.), antibiotics; organic acids and amino acids (methionine, lysine, . . . ). The active ingredients will preferably make up a proportion of 0.001 to 20% by weight, particularly preferably from 0.01 to 5% by weight, of the by-product (based on the dry matter).

The examples hereinafter serve to illustrate the invention, but are not to be understood as being restrictive.

The abbreviation DM used in the examples means dry matter.

The experiments described in examples 1 to 4 hereinafter for liquefaction/saccharification were carried out in a laboratory stirred tank having 0.75 L working volume. The laboratory stirred tank was mixed using a horseshoe-shaped agitator. The viscosity in the stirred tank was determined online from the torque and the speed of rotation of the agitator motor. The temperature in the stirred tank was measured by a Pt100 temperature sensor and adjusted via an external oil bath via a jacket of the stirred tank. The pH measurement was made via an Ag/AgCl electrode. The pH was adjusted using 50% strength NaOH or 50% strength $H_2SO_4$.

EXAMPLE 1

Liquefying and Saccharifying a Wholegrain Flour

In the experiments hereinafter a wheat wholegrain flour was used. The wheat wholegrain flour had the following characteristic composition:

11.2% by weight of water
13% by weight of crude protein
1.8% by weight of crude fat
2.1% by weight of crude fiber
1.7% by weight of ash
70.2% by weight of nitrogen-free extract (carbohydrates)

The median particle size of the flour was 54 μm.

Experiment 1:

For one batch of 800 g in the laboratory stirred tank, 6.06 ml of Shearzyme 500L (Novozymes A/S, Denmark; xylanase having 2.0% by weight based on the DM of the flour used) and 0.288 ml of Liquozyme SD CS (Novozymes A/S, Denmark; α-amylase having 0.1% by weight based on the DM of the flour used) were charged together with 386 g of water in the stirred tank and preheated to 58° C. In total, 414 g of the described wholegrain flour were placed in the batch (46% by weight total DM content), wherein the addition took place in two steps. In a first step, 293 g were added. After the pH was adjusted to pH 5.0 using 50% strength $H_2SO_4$, the suspension was incubated for 1 h. After the pH was adjusted to 5.5-5.8 using 50% strength NaOH, the mixture was then heated to 85° C. and the remaining amount of the flour was added. Subsequently the tank contents were heated for 10 min to 100° C. and then cooled again to 85° C. After renewed monitoring and adjustment of the pH to 5.5-5.8, 0.288 ml of Liquozyme SD CS were added additionally. Under these conditions, the tank contents were stirred until an iodine-starch test gave a negative result. Then the reactor contents were cooled down to 60° C. and the pH was adjusted to pH 4.3 by 50% strength $H_2SO_4$. By adding 4.75 ml of Dextrozyme GA (Novozyme A/S, Denmark; glucoamylase having 1.5% by weight based on the DM of the flour used), the saccharification was started. After saccharification for 2 hours, the reactor contents were briefly heated to 100° C. for deactivation of the glucoamylase.

Corresponding to the added amounts, 36% by weight of starch were in the batch. In a concluding glucose analysis, 338 g/l of glucose were determined. The median viscosity during liquefaction was 0.22 Pa·s, and during the saccharification 0.25 Pa·s.

Experiment 2:

In a further experiment, in total 487 g of flour were used in an 800 g batch in a similar manner to experiment 1. The starch proportion in the batch, at a total DM content of 54% by weight, was therefore 43% by weight. The amounts of enzymes used were adapted in the experiment in accordance with the higher DM content. For a similar experimental procedure, a glucose concentration of 342 g/l was achieved. The median viscosity during liquefaction was 1.31 Pa·s, and during saccharification 0.98 Pa·s.

EXAMPLE 2

Liquefying and Saccharifying a Wheat Flour Without Bran

In the experiments hereinafter, a wheat flour substantially freed from bran components by fractional dry milling was used. The wheat flour had the following characteristic composition:
11.3% by weight of water
12% by weight of crude protein
1.2% by weight of crude fat
0.8% by weight of crude fiber
0.8% by weight of ash
73.9% by weight of nitrogen-free extracts (carbohydrates)
The median particle size of the flour was 55 μm.

Corresponding to the procedure described in example 1, various amounts of this flour were liquefied and saccharified each in 800 g batches. The amounts of flour used, the resultant starch content, the measured glucose concentration and also the measured median viscosities during liquefaction and saccharification are shown in table 1.

TABLE 1

Glucose concentration and viscosity depending on the total dry matter and starch dry matter contents

| | | | | | Median viscosity | |
|---|---|---|---|---|---|---|
| # | Flour [g] | Total DM [% by wt.] | Starch DM [% by wt.] | Glucose [g/l] | LF [Pa·s] | SC [Pa·s] |
| 1 | 361 | 40 | 33 | 330 | 0.05 | 0.09 |
| 2 | 424 | 47 | 39 | 384 | 0.07 | 0.10 |
| 3 | 487 | 54 | 45 | 437 | 0.67 | 0.55 |

LF: liquefaction
SC: saccharification

EXAMPLE 3

Liquefying and Saccharifying Wheat Starch

In the experiments hereinafter, a wheat starch was used, for the production of which first, a wheat flour substantially freed from bran components was produced by fractional dry milling of wheat grains, which was subsequently, in a conventional manner, freed from gluten components and dried. The wheat starch had the following characteristic composition:
10.8% by weight of water
0.9% by weight of crude protein
0.2% by weight of crude fat
0.3% by weight of crude fiber
0.3% by weight of ash
87.5% by weight of nitrogen-free extract (carbohydrates)
The median particle size of the fraction was 27 μm.

Corresponding to the procedure described in example 1, various amounts of this wheat starch were liquefied and saccharified each time in 800 g batches. The amounts used of wheat starch, the resultant starch content in the suspension, the measured glucose concentration and also the measured median viscosities during liquefaction and saccharification are shown in table 2.

TABLE 2

Glucose concentration and viscosity depending on the total dry matter and starch dry matter content

| | | | | | Median viscosity | |
|---|---|---|---|---|---|---|
| # | Starch [g] | Total DM [% by wt.] | Starch DM [% by wt.] | Glucose [g/l] | LF [Pa·s] | SC [Pa·s] |
| 1 | 233 | 26 | 26 | 233 | 0.001 | 0.01 |
| 2 | 251 | 28 | 27 | 266 | 0.025 | 0.048 |
| 3 | 287 | 32 | 31 | 276 | 0.026 | 0.048 |
| 4 | 332 | 37 | 36 | 399 | 0.017 | 0.073 |

LF: liquefaction
SC: saccharification

EXAMPLE 4

Liquefying and Saccharifying a Mixture of Bran-Free Wheat Flour and Wheat Starch Corresponding to the procedure described in example 1, various mixtures of the wheat flour of example 2 and the wheat starch of example 3 were liquefied and saccharified each time in 800 g batches. The amounts used of wheat starch, the resultant starch content in the suspension, the measured glucose concentration and also the measured median viscosities during liquefaction and saccharification are shown in table 2.

Corresponding to the procedure described in example 1, various mixtures of bran-free wheat flour (see example 2) and wheat starch (see example 4) were liquefied and saccharified each time in 800 g batches. The amounts used of the two starch sources, the resultant total dry matter and starch contents, the measured glucose concentration and also the measured median viscosities during liquefaction and saccharification are shown in table 2.

TABLE 3

Glucose concentration and viscosity depending on the total dry matter and starch dry matter contents

| # | Flour WF [g] | WS [g] | Total DM [% by wt.] | Starch DM [% by wt.] | Glucose [g/L] | Median viscosity LF [Pa·s] | SC [Pa·s] |
|---|---|---|---|---|---|---|---|
| 1 | 111 | 219 | 37 | 34 | 363 | 0.006 | 0.010 |
| 2 | 207 | 188 | 44 | 40 | 404 | 0.009 | 0.034 |
| 3 | 303 | 158 | 51 | 45 | 436 | 0.144 | 0.152 |

WF: bran-free wheat flour,
WS: wheat starch
LF: liquefaction
SC: saccharification

EXAMPLE 5

Gluten Removal from the Wholegrain Wheat Flour Hydrolyzate of Example 1

The solids fraction was separated off from the wholegrain wheat flour hydrolyzate having 338 g/l glucose concentration which was produced in example 1, experiment 1 and washed to decrease the glucose loss. For this, 10 g of the hydrolyzate were heated to and maintained at 40° C. and the pH was adjusted to 4.3 and then the mixture was separated on a Rotana 96 RSC laboratory centrifuge at 1650 g in the course of 15 min. In the course of this 2.73 g of supernatant formed having a glucose concentration of 357 g/l and 7.27 g of pellet formed having a glucose concentration of 307 g/l.

The resultant pellet was then resuspended with 9.68 g of deionized water and centrifuged again (25° C., 1650 g). In the course of this a second supernatant of 10.67 g formed having a glucose concentration of 137 g/l and a pellet of 6.28 g formed having a glucose concentration of 108 g/l.

The resultant solids were dried and analyzed, wherein the following composition resulted:
7.7% by weight of water
32.3% by weight of crude protein
4.0% by weight of crude fat
6.2% by weight of crude fiber
1.4% by weight of ash
48.4% by weight of nitrogen-free extract (carbohydrates)

The resultant glucose solution had the following composition based on dry matter:
93.4% by weight of sugar
4.0% by weight of crude protein
0.1% by weight of crude fibers
0.03% by weight of free amino acids
1.0% by weight of crude ash

EXAMPLE 6

Gluten Removal from the Hydrolyzate of Example 2

From the wheat flour hydrolyzate produced in example 2, experiment No. 1, having a glucose concentration of 330 g/l, the solids fraction was removed and washed to decrease the glucose loss. For this, 10 g of the hydrolyzate were heated to and maintained at 40° C. and the pH was adjusted to 4.3 and then the mixture was separated on a Rotana 96 RSC laboratory centrifuge at 1650 g in the course of 15 min. In the course of this 5.58 g of supernatant formed having a glucose concentration of 350 g/l and 4.41 g of pellet formed having a glucose concentration of 304 g/l.

The resultant pellet was then resuspended with 6.19 g of deionized water and centrifuged again (25° C., 1650 g). In the course of this a second supernatant of 6.75 g formed having a glucose concentration of 132 g/l and a pellet of 3.85 g formed having a glucose concentration of 115 g/l.

The resultant solids were dried and analyzed, wherein the following composition resulted:
8.8% by weight of water
38.5% by weight of crude protein
2.6% by weight of crude fat
2.1% by weight of crude fiber
0.8% by weight of ash
47.2% by weight of nitrogen-free extract (carbohydrates)

The resultant glucose solution had the following composition based on dry matter:
94.1% by weight of sugar
2.9% by weight of crude protein
0.1% by weight of crude fibers
0.02% by weight of free amino acids
0.5% by weight of crude ash

EXAMPLE 7

Gluten Removal from the Hydrolyzate of Example 4

From the hydrolyzate produced in example 4 experiment No. 2, of a wheat flour/wheat starch mixture having a glucose concentration of 404 g/l, the solids fraction was removed and washed to decrease the glucose loss. For this, 10 g of the hydrolyzate were heated to and maintained at 40° C. and the pH was adjusted to 4.3 and then the mixture was separated on a Rotana 96 RSC laboratory centrifuge at 1650 g in the course of 15 min. In the course of this 5.01 g of supernatant formed having a glucose concentration of 411.5 g/l and 4.98 g of pellet formed having a glucose concentration of 385 g/l.

The resultant pellet was then resuspended with 5.85 g of deionized water and centrifuged again (25° C., 1650 g). In the course of this a second supernatant of 7.62 g formed having a glucose concentration of 178 g/l and a pellet of 3.21 g formed having a glucose concentration of 158 g/l.

The resultant solids were dried and analyzed, wherein the following composition resulted:
6.4% by weight of water
28.3% by weight of crude protein
3.0% by weight of crude fat
1.3% by weight of crude fiber
1.5% by weight of ash
59.5% by weight of nitrogen-free extract (carbohydrates)

The resultant glucose solution had the following composition based on dry matter:
94.3% by weight of sugar
2.3% by weight of crude protein
0.11% by weight of crude fibers
0.01% by weight of free amino acids
0.3% by weight of crude ash

EXAMPLE 8

Concentrating the Hydrolyzate

Corresponding to the procedure in example 2, a hydrolyzate was produced by liquefying and saccharifying the wheat flour used in example 2. The solids were then removed therefrom in a similar manner to example 6 by centrifugation, resuspension (washing) and repeated centrifugation. By combining the supernatant from the first solids removal and after washing, 575 g of a solution were produced which comprised 21.8% by weight of glucose. From this solution, 366 g of water were evaporated off in a rotary evaporator at 80° C. and a pressure between 220 and 160 mbar. There remained in the rotary evaporator 209 g of a 60% strength glucose solution. Under the chosen conditions, no deposition on the inside of the rotary evaporator was observed. The solution produced had, at 60° C., a viscosity of 0.4 Pa·s (Haake RheoStress1, 100 s$^{-1}$ shear rate). The glucose solution thus concentrated was subsequently used in a fermentation.

EXAMPLE 9

Use of the Glucose Solutions Produced in Fermentations

All fermentations were carried out using a genetically modified strain of Corynebacterium glutamicum. An exact description on strain ATCC13032 lysC$^{fbr}$ may be found in WO 2005/116228. The cells were incubated overnight at 30° C. on sterile CM agar plates (for media composition see table 3, sterilized for 20 min at 121° C.) and then resuspended in 0.9% strength NaCl solution. From this suspension, then appropriate volumes were inoculated in shake flasks in such a manner than an optical density of 1.5 at 610 nm is achieved.

TABLE 3

Composition of the CM agar medium for 1 l of medium

| Component | Amount |
| --- | --- |
| Peptone | 10 g |
| Beef extract | 5 g |
| Yeast extract | 5 g |
| NaCl | 2.5 g |
| Agar | 25 g |
| 40% strength by weight glucose* | 25 ml |
| Urea (40 g/l)* | 50 ml |

*sterile-filtered at 120° C., 20 min

The shake flask experiments were carried out in 100 ml Erlenmeyer flasks having 10 ml working volumes. The shaking experiments were carried out for 48 h at 30° C., 200 min$^{-1}$ and 80% relative humidity.

The composition of the shake flask medium is given in table 4. For the control medium, all media components except for the vitamin solution were dissolved together in 1 l of water. The pH of the medium was adjusted to 7.8 using ammonium hydroxide and the medium was subsequently sterilized at 121° C. for 20 min. The vitamin solution was sterile-filtered (0.2 µm) after the sterilization and added. When wheat flour hydrolyzates were used, glucose in table 4 was replaced by a corresponding amount of glucose solution. The other components were dissolved in 600 ml of water in order to be able to add an amount of wheat flour hydrolyzate corresponding to 60 g of glucose. When wheat flour hydrolyzate was used sterile water was used to make up the medium.

TABLE 4

Composition of the main medium for 1 l of medium

| Component | Amount |
| --- | --- |
| Glucose | 60 g |
| Ammonium sulfate | 20 g |
| MgSO$_4$·7H$_2$O | 0.8 g |
| KH$_2$PO$_4$ | 0.6 g |
| Yeast extract | 10 g |
| CaCO$_3$ | 50 g |
| FeSO$_4$ solution (2 mg/ml) | 1 ml |
| MnSO$_4$ solution (2 mg/ml) | 1 ml |
| Vitamin solution | 5000 µl |

Corresponding to examples 1, 2 and 4 for liquefaction and saccharification, and also examples 5 to 7 for gluten removal, glucose solutions having the following glucose concentrations were produced:

Glucose solution 1: 251 g/l of hydrolyzate of example 2, experiment No. 1, gluten depletion in a similar manner to example 6.

Glucose solution 2: 186 g/l of hydrolyzate of example 1, experiment No. 1, gluten depletion in a similar manner to example 5.

Glucose solution 3: 266 g/l of hydrolyzate of example 4, experiment No. 2, gluten depletion in a similar manner to example 7.

Duplicate experiments resulted respectively in lysine concentrations of 8.08 g/l (control, pure glucose), 8.48 g/l (glucose solution 2), 8.36 g/l (glucose solution 1) and 10.75 g/l (glucose solution 3).

The invention claimed is:

1. A method for producing an aqueous glucose solution having a glucose content of at least 32% by weight from starch of wheat grains of Triticeae plants, comprising: a) fractionating dry milling of wheat grains of Triticeae plants to obtain a milled material, wherein the grains are separated into a starch-comprising endosperm fraction and a bran fraction, and wherein said milled material comprises essentially the starch-comprising endosperm fraction; b) converting the endosperm fraction milled material into an aqueous suspension, wherein the aqueous suspension comprises 30 to 55% by weight of starch based on total weight of the aqueous suspension; and c) enzymatically liquefying and enzymatically saccharifying the starch of the aqueous suspension to obtain an aqueous glucose solution, wherein the aqueous glucose solution has a glucose content of at least 32% by weight; and wherein gluten present in the endosperm fraction is depleted from the aqueous glucose solution obtained in step c) and/or from the aqueous suspension of the endosperm fraction before carrying out step c).

2. The method according to claim 1, wherein the milling in step a) is carried out in the presence of 10 to 30% by weight of water based on the mass of the grains used.

3. The method according to claim 1, wherein, in step a), the endosperm fraction is milled to a median particle size in the range from 0.01 to 1.0 mm.

4. The method according to claim 1, wherein at least 70% of the gluten is separated off, based on total gluten present in the endosperm fraction used.

5. The method according to claim 1, wherein at least some of the gluten of the endosperm fraction is depleted from the aqueous glucose solution obtained in step c).

6. The method according to claim 1, wherein some of the gluten of the endosperm fraction is depleted before carrying out step c).

7. The method according to claim 6, wherein depleting the gluten before carrying out step c) comprises the following substeps:

i) converting some of the endosperm fraction into a dilute aqueous suspension of the endosperm fraction having a starch content of less than 30% by weight;

ii) depleting the gluten from the dilute aqueous suspension of the endosperm fraction to obtain a gluten-depleted dilute aqueous suspension of the endosperm fraction; and iii) suspending the remainder of the endosperm fraction in the gluten-depleted dilute aqueous suspension obtained in step ii) to obtain an aqueous suspension comprising a starch content of at least 30% to 50% by weight.

8. The method according to claim 6, wherein the remainder of the gluten of the endosperm fraction is depleted from the aqueous glucose solution obtained in step c).

9. The method according to claim 1, wherein the gluten is depleted in such a manner that the aqueous glucose solution comprises less than 10% by volume of solids.

10. A method for producing an organic substance by fermentation, which comprises the following steps:
   i. providing a glucose solution by a method according to claim 1 and
   ii. adding the glucose solution to a fermentation medium which comprises a microorganism which is capable of overproduction of the organic substance.

11. The method according to claim 10, wherein the organic substance is selected from optionally hydroxyl-bearing mono-, di- and tricarboxylic acids having 3 to 10 carbon atoms, proteinogenic and non-proteinogenic amino acids, purine bases, pyrimidine bases; nucleosides, nucleotides, lipids, saturated and unsaturated fatty acids, diols having 4 to 10 carbon atoms, polyhydric alcohols having 3 or more hydroxyl groups, long-chain alcohols having at least 4 carbon atoms, carbohydrates, aromatic compounds, vitamins, provitamins, cofactors, nutraceuticals, proteins, yeasts, carotenoids, ketones having 3 to 10 carbon atoms, lactones, polyhydroxyalkanoates, polylactides, polysaccharides, polyisoprenoids, polyamides and cyclodextrins.

12. The method according to claim 11, wherein the organic substance is an amino acid.

13. The method according to claim 12, wherein the amino acid is selected from lysine, methionine, threonine and glutamate.

14. The method according to claim 11, wherein the organic substance is selected from vitamins and provitamins.

15. The method according to claim 11, wherein the organic substance is selected from aliphatic mono-, di- and tricarboxylic acids having 2 to 10 carbon atoms.

16. The method according to claim 11, wherein the organic substance is selected from aliphatic hydroxycarboxylic acids having 3 to 10 carbon atoms.

17. The method according to claim 11, wherein the organic substance is selected from alkanediols having 3 to 10 carbon atoms.

18. The method according to claim 11, wherein the organic substance is selected from aliphatic ketones having 3 to 10 carbon atoms.

19. The method according to claim 11, wherein the organic substance is selected from aliphatic diamines having 3 to 10 carbon atoms.

20. The method according to claim 11, wherein the organic substance is selected from nucleotides.

21. The method according to claim 11, wherein the organic substance is selected from disaccharides, oligosaccharides and polysaccharides.

22. The method according to claim 10, wherein the biomass resulting from the microorganism is separated off from the overproduced organic substance of the fermentation product, and wherein a biomass-comprising composition is obtained.

23. A method for producing an organic substance by a reaction not involving fermentation, comprising
   i) providing an aqueous solution according to claim 1; and
   ii) using the thus obtained glucose solution or an essentially water-free glucose obtained by concentrating said glucose solution to a water content of less than 10% by weight in a reaction not involving fermentation for producing the desired organic substance.

* * * * *